(12) United States Patent
Alenfall et al.

(10) Patent No.: US 9,381,149 B2
(45) Date of Patent: Jul. 5, 2016

(54) COMPOSITIONS AND USES THEREOF

(75) Inventors: Jan Alenfall, Lomma (SE); Pontus Duner, Lund (SE); Anna Hultgardh Nilsson, Genarp (SE)

(73) Assignee: FOLICUM, AB, Lund (SE)

( * ) Notice: Subject to any disclaimer, the term of this patent is extended or adjusted under 35 U.S.C. 154(b) by 120 days.

(21) Appl. No.: 14/237,108

(22) PCT Filed: Aug. 10, 2012

(86) PCT No.: PCT/GB2012/051955
§ 371 (c)(1),
(2), (4) Date: Sep. 5, 2014

(87) PCT Pub. No.: WO2013/021212
PCT Pub. Date: Feb. 14, 2013

(65) Prior Publication Data
US 2015/0018273 A1 Jan. 15, 2015

(30) Foreign Application Priority Data
Aug. 10, 2011 (GB) .................................. 1113770.0

(51) Int. Cl.
| | | |
|---|---|---|
| *A61Q 7/00* | (2006.01) | |
| *A61K 8/64* | (2006.01) | |
| *A61K 38/18* | (2006.01) | |
| *A61K 38/04* | (2006.01) | |
| *C07K 14/475* | (2006.01) | |
| *A61K 38/17* | (2006.01) | |
| *A61K 38/19* | (2006.01) | |

(52) U.S. Cl.
CPC . *A61K 8/64* (2013.01); *A61K 38/17* (2013.01); *A61K 38/19* (2013.01); *A61Q 7/00* (2013.01); *A61K 2800/74* (2013.01)

(58) Field of Classification Search
None
See application file for complete search history.

(56) References Cited

U.S. PATENT DOCUMENTS

| | | | |
|---|---|---|---|
| 5,756,094 A | 5/1998 | Lavker et al. | |
| 7,504,232 B2 | 3/2009 | Barry et al. | |
| 7,662,633 B2 | 2/2010 | Barry et al. | |

FOREIGN PATENT DOCUMENTS

| | | |
|---|---|---|
| WO | 9632961 | 10/1996 |
| WO | 0171358 | 9/2001 |
| WO | EP1375518 | 1/2004 |
| WO | 2005066339 | 7/2005 |
| WO | 2008086449 | 7/2008 |

OTHER PUBLICATIONS

Xuan et al. Site-Directed Mutagenesis of the Arginine-Glycine-Aspartic Acid Sequence in Osteopontin Destroys Cell Adhesion and Migration Functions. Journal of Cellular Biochemistry 57:680-690 (1995).*
Wells, J.A. Additivity of Mutational Effects in Proteins. Biochemistry 29:8509-8517 (1990).*
Ngo et al. Computational Complexity, Protein Structure Prediction and the Levinthal Paradox. The Protein Folding Problem and Tertiary Structure Prediction, pp. 433-440 and 492-495 (1994).*
Oldberg et al., "Cloning and sequence analysis of rat bone sialoprotein (osteopontin) cDNA reveals an Arg-Gly-Asp cell-binding sequence," Proceedings of the National Academy of Sciences, 1986, 8819-8823, 83(23).
Scatena et al., "Osteopontin: a multifunctional molecule regulating chronic inflammation and vascular disease," Arteriosclerosis, Thrombosis, and Vascular Biology, 2007, 2302-2309, 27.
Courter et al., "The RGD domain of human osteopontin promotes tumor growth and metastasis through activation of survival pathways," PLoS One, 2010, 1-11, 5(3).
Katagiri et al., "Non-RGD domains of osteopontin promote cell adhesion without involving alpha v integrins," Journal of Cellular Biochemistry, 1996, 123-131, 62.
Yu et al., "Osteopontin gene is expressed in the dermal papilla of pelage follicles in a hair-cycle-dependent manner," Journal of Investigative Dermatology, 2001, 1554-1558, 117.
Franzen et al. "Isolation and characterization of two sialoproteins present only in bone calcified matrix," Journal of Biochemistry, 1985, 715-724, 232(3).

* cited by examiner

*Primary Examiner* — Elizabeth C Kemmerer
*Assistant Examiner* — Regina M Deberry
(74) *Attorney, Agent, or Firm* — Robert C. Netter, Jr.; Dann, Dorfman, Herrell & Skillman

(57) ABSTRACT

The present invention provides a composition for stimulating hair growth in a mammal comprising a modified osteopontin polypeptide in which an RGD domain is inactivated; and a pharmaceutically acceptable and/or cosmetically acceptable excipient, carrier or diluent. The invention further provides methods of stimulating hair growth in a mammal.

8 Claims, 9 Drawing Sheets

COMPOSITIONS AND USES THEREOF

This application is a §371 application of PCT/GB2012/051955, filed Aug. 10, 2012, which in turn claims priority to GB Application 1113770.0, filed Aug. 10, 2011. The entire disclosure of each of the foregoing applications is incorporated by reference herein.

FIELD OF INVENTION

The present invention relates to agents for stimulating hair growth in mammals. In particular, there are provided compositions comprising a modified osteopontin polypeptide, and the pharmaceutical and cosmetic use thereof for stimulating hair growth in mammals (including humans).

BACKGROUND

Hair growth is cyclical, occurring in three stages: anagen, the active growth phase; catagen, the degenerative phase; and telogen, the resting phase. After telogen, the old hair fibre is shed and a new hair is generated as part of the repeating cycle.

Alopecia, or hair loss, occurs in both men and women, and is attributed to numerous causes including aging, hormone levels, stress, and chemotherapy. In these circumstances, more and more hair follicles remain in the telogen stage, resulting in a gradual decrease of the hair fibre length and diameter, finally reaching a stage of partial or complete baldness.

Various types of hair loss are known, including alopecia areata, androgenetic alopecia, anagen effluvium, self-induced hair loss, telogen effluvium, and scarring alopecia. Alopecia areata, thought to be an auto-immune disorder, begins with hair loss in a rounded patch on the scalp. Alopecia areata includes mild patchy hair loss on the scalp, as well the loss of all scalp hair, known as alopecia totalis, and the loss of all scalp and body hair, known as alopecia universalis. Androgenetic alopecia, including male and female pattern baldness, is thought to be caused by a combination of genetic predisposition, aging, and androgen hormone levels. Androgenetic alopecia is associated with increased androgen stimulation, which adversely affects the hair follicles.

Increased androgen stimulation can be produced by, among other mechanisms, elevated levels of 5-alpha-reductase, an enzyme that converts testosterone to dihydrotestosterone. Anagen effluvium is hair loss due to chemicals or radiation, such as chemotherapy or radiation treatment for cancer. Self-induced hair loss includes hair loss caused by conscious or unconscious self-inflicted damage to the hair. Two common types of self-induced hair loss are trichotillomania, or hair loss that results when someone continually pulls or plucks out his own hair, and traction alopecia, which is caused by hairstyles such as ponytails or braids that continually pull at the hair. Telogen effluvium is stress-related hair loss caused by events such as, for example, surgery, child birth, or pregnancy termination. Further causes of telogen effluvium include the use of oral contraceptives or other prescription drugs, thyroid abnormality, diabetes, lupus, and emotional stress. Scarring alopecia includes hair loss caused by infection and inflammation of the hair follicles, and hair loss caused by burns or other trauma.

Hair loss is a widespread problem that is considered by some to be cosmetically unappealing and often causes emotional distress to the individual concerned. As a consequence, there is great demand for alopecia treatments. Many compositions have been tested for their ability to stimulate hair growth, for example, by promoting or prolonging anagen. Examples of such compositions include potassium channel openers, such as minoxidil (Regaine®, Pharmacia Corp.) and diazoxide; 5-alpha-reductase inhibitors, such as finasteride (Propecia®, Merck & Co.); and the immunosuppressant cyclosporin A.

However, such known treatments for stimulating hair growth exhibit limited effectiveness and cause unwanted side effects. For example, among other undesirable side effects, potassium channel openers cause cardiovascular effects, finasteride is unsafe for women who are pregnant or may become pregnant, and cyclosporin A suppresses the immune system. Further, even when applied topically to areas in which hair growth is desired, known treatments for alopecia often cause hair growth in undesired areas of the body, such as facial hair on women. Such disadvantages of known compositions for treating alopecia lead many individuals experiencing hair loss to rely on wigs and toupees. Other individuals seek hair transplant surgery, which is expensive, is not fully effective, and sometimes is not possible, for example, for chemotherapy patients.

Accordingly, there is a need for new treatments to stimulate hair growth, suitable for use in both medical and cosmetic applications.

SUMMARY OF INVENTION

The first aspect of the invention provides a composition for stimulating hair growth in a mammal comprising:
(a) a modified osteopontin polypeptide in which an RGD domain is inactivated; and
(b) a pharmaceutically acceptable and/or cosmetically acceptable excipient, carrier or diluent.

Thus, the active component of the compositions of the invention is derived from a naturally-occurring osteopontin protein (i.e. the polypeptide comprises an amino acid sequence corresponding to that of a modified, for example mutated, version of a naturally-occurring osteopontin protein).

Osteopontin, also known as bone sialoprotein I (BSP-1 or BNSP), early T-lymphocyte activation (ETA-1), secreted phosphoprotein 1 (SPP1), 2ar and *Rickettsia* resistance (Ric), is a gene product which is conserved in several mammalian species.

The gene has seven exons, spans 5 kilobases in length and in humans it is located on the long arm of chromosome 4 region 13 (4q13). The protein is composed of ~300 amino acids residues and is rich in acidic residues: 30-36% are either aspartic or glutamic acid. Osteopontin has ~30 attached carbohydrate residues, including 10 sialic acid residues, which are attached to the protein during post-translational modification in the Golgi apparatus.

Osteopontin was first discovered as a novel sialoprotein in bone anchoring osteoclasts onto the mineralized bone matrix (Franzen & Heinegard, 1985, *Biochem. J.* 232(3)715-24). The name osteopontin comes from the presence of the protein in bone (osteo-) and its ability to form a bridge (-pons) between bone cells and the mineral phase. Sequence analysis and subsequent structural studies showed osteopontin to be a 32 kDa glycoprotein composed of a highly acidic region of some ten aspartic acid residues thought to mediate the mineral binding properties of osteopontin. Furthermore, in the mid portion of the osteopontin molecule there is also a cell attachment domain mediated through an R-G-D sequence (Oldberg et al., 1986, *Proc. Natl. Acad. Sci.* USA 83(23): 8819-23).

Osteopontin is constitutively expressed in osteoblasts and in several epithelial cell types, resulting in osteopontin being secreted into many body fluids. Bone is the only tissue type where osteopontin is deposited and from where it can be recovered in large amounts. The expression of osteopontin can also be induced in vascular smooth muscle cells, in different cancer cell types and among inflammatory cells (specifically macrophages and T lymphocytes). Several important cellular functions have been attributed to osteopontin such as adhesion, proliferation, migration, anti-apoptosis and chemo attraction. Some of these functions are believed to be mediated via the RGD cell-adhesion domain which interacts with different integrins, mainly with αvβ3 but also αvβ1, and αvβ5 (for review see Scatena et al., 2007, *Arterio. Thromb. Vasa Biol.* 27:2302-2309).

In recent years, osteopontin has emerged as a potent cytokine capable of modulating several cell types involved in inflammation and immune responses. The broad range of functions being attributed to osteopontin has been puzzling and cannot all be explained by the single cell-binding RGD sequence. The explanation came when an eleven amino acid peptide in osteopontin $R^{145}$-G-D-S-L-A-Y-G-L-R-$S^{155}$ (SEQ ID NO:122) (corresponding to amino acids 144 to 154 of UniProt code P10923) was identified and later functionally mapped. In addition to the known $R^{145}$-G-$D^{147}$ site mediating binding to the αvβ3 integrin, two additional essential regions in the osteopontin molecule were discovered, namely a highly specific thrombin cleavage site, i.e. $R^{154}$-$S^{155}$, and a cryptic integrin binding site, i.e. $S^{148}$-L-A-Y-G-L-$R^{154}$ (SEQ ID NO:123), which binds to an α9β1 integrin (see Scatena et al., supra). An additional binding site for α4β1 has also been identified (see Scatena et al., supra).

A characterising feature of the osteopontin-derived polypeptide in the compositions of the invention is that the RGD domain naturally present in osteopontin is inactivated such that it is non-functional (at least in part). For example, inactivation of the RGD domain may prevent the osteopontin-derived polypeptide from binding to one or more of the integrins which bind the naturally occurring osteopontin protein.

Thus, by "modified osteopontin polypeptide" we include polypeptides corresponding to a modified form of a naturally-occurring osteopontin protein in which the RGD domain is non-functional (at least in part), as well as fragments and variants thereof which retain a hair-stimulatory property of the 'full length' modified osteopontin. For example, the non-functional RGD domain of the modified osteopontin polypeptide may be unable to bind integrin αvβ3 (see Scatena et al., supra).

Advantageously, the naturally-occurring osteopontin protein is mammalian, e.g. human.

The modified osteopontin polypeptides present in the compositions of the invention are capable of stimulating hair growth in mammals.

In one embodiment, the polypeptide is capable of stimulating the growth of human hair.

In a further embodiment, the polypeptide is capable of stimulating the growth of hair in vivo.

In a further embodiment, the polypeptide is capable of stimulating the growth of hair in vivo with greater efficacy than wildtype human osteopontin. By "greater efficacy" in this context, we include a quicker onset of action and/or efficacy at a lower dose and/or greater maximum effect (e.g. greater number of new follicles or density of hair). In one embodiment, the polypeptide is capable of stimulating the growth of hair in vivo with a quicker onset of action and a greater maximum hair growth effect than wildtype human osteopontin at the same dose (e.g. see Example B).

It will be appreciated by persons skilled in the art that the stimulation of hair growth may be mediated by an effect of existing hair follicles and/or by inducing the formation of new hair follicles.

Thus, in one embodiment, the modified osteopontin polypeptide is capable of stimulating existing hair follicles (for example, by prolonging the anagen phase and/or by shortening the telogen phase such that the resting follicles become active).

In a further embodiment, the polypeptide is capable of inducing the formation of new hair follicles, or stem cells for producing the same.

Naturally-occurring osteopontin proteins are typically around 300 amino acids in length. However, it will be appreciated by persons skilled in the art that the modified osteopontin polypeptides present in the compositions of the invention may vary from this length.

Typically, the polypeptide is fewer than 500 amino acids in length, for example fewer than 400, 350, 340, 330, 320, 310, 300, 290, 280, 270, 260, 250, 200, 150, 100, 50, 40, 30, 20, 15, 10 or fewer amino acids in length.

In one embodiment, the polypeptide is between 250 and 350 amino acids in length, for example between 280 and 300 amino acids in length (e.g. 293 amino acids in length).

In an alternative embodiment, the polypeptide is between 10 and 20 amino acids in length, for example between 12 and 18 amino acids in length (e.g. 15 amino acids in length).

As discussed above, the modified osteopontin polypeptides lack the active tri-peptide sequence "arginine-glycine-aspartic acid" normally found in naturally-occurring osteopontin proteins. It will be appreciated that this RGD domain may be inactivated by a number of different strategies.

In one embodiment, the RGD domain is mutated at one or more amino acids in the modified osteopontin polypeptide, such that it contains one or more deletions, substitutions and/or additions, or combinations thereof, relative to a naturally-occurring osteopontin protein.

For example, the RGD domain may be deleted, at least in part, such that the arginine and/or glycine and/or aspartic acid residue is absent.

Alternatively, or in addition, the RGD domain may be substituted at one or more amino acids. For example, the arginine and/or glycine and/or aspartic acid residue may be substituted with another amino acid. Such substitutions may be conservative or non-conservative.

Likewise, the RGD domain may be inactivated by a combination of substitutions and deletions, including:
(a) substitution of the arginine residue and deletion of the glycine and aspartic acid residues;
(b) substitution of the arginine and glycine residues and deletion of the aspartic acid residue (for example, the -RGD- tripeptide can be replaced with the dipeptide sequence -DI-);
(c) substitution of the arginine and aspartic acid residues and deletion of the glycine residue; or
(d) deletion of the arginine and aspartic acid residues and substitution of the glycine residue.

In one embodiment, the tripeptide -RGD- sequence is replaced by the dipeptide -DI- sequence.

Without wishing to be bound by theory, it is believed that inactivation of the RGD sequence may result in a conformational change in the osteopontin polypeptide (relative to the corresponding naturally-occurring osteopontin protein), which leads to the creation/exposure of a new site to the surrounding milieu.

In one preferred embodiment, the modified osteopontin polypeptide comprises or consists of the amino acid sequence of SEQ ID NO:1 (in which the region encompassing the inactivated RGD domain is underlined):

```
                                             SEQ ID NO: 1
MRLAVICFCLFGIASSLPVKVTDSGSSEEKLYSLHPDPIATWLVPDPSQK

QNLLAPQNAVSSEEKDDFKQETLPSNSNESHDHMDDDDDDDDDGDH

AESEDSVDSDESDESHHSDESDETVTASTQADTFTPIVPTVDVPNGDISL

AYGLRSKSRSFQVSDEQYPDATDEDLTSHMKSGESKESLDVIPVAQLLS

MPSDQDNNGKGSHESSQLDEPSLETHRLEHSKESQESADQSDVIDSQA

SSKASLEHQSHKFPHSHKDKLVLDPKSKEDDRYLKFRISHELESSSSEVN
``` or a fragment, variant, derivative or fusion thereof (or a fusion of said fragment, variant or derivative) which retains (at least in part) a hair growth stimulatory activity of the amino acid sequence of SEQ ID NO:1.

The term 'amino acid' as used herein includes the standard twenty genetically-encoded amino acids and their corresponding stereoisomers in the 'D' form (as compared to the natural 'L' form), omega-amino acids and other naturally-occurring amino acids, unconventional amino acids (e.g., α,α-disubstituted amino acids, N-alkyl amino acids, etc.) and chemically derivatised amino acids (see below).

When an amino acid is being specifically enumerated, such as 'alanine' or 'Ala' or 'A', the term refers to both L-alanine and D-alanine unless explicitly stated otherwise. Other unconventional amino acids may also be suitable components for polypeptides of the present invention, as long as the desired functional property is retained by the polypeptide. For the polypeptides shown, each encoded amino acid residue, where appropriate, is represented by a single letter designation, corresponding to the trivial name of the conventional amino acid.

In accordance with convention, the amino acid sequences disclosed herein are provided in the N-terminus to C-terminus direction.

Typically, the modified osteopontin polypeptides used in the compositions of the invention comprise or consist of L-amino acids.

In one embodiment, the polypeptide may comprise or consist of a fragment of the amino acid sequence of SEQ ID NO: 1, or a variant thereof.

By "fragment" we include at least 6 contiguous amino acids of the amino acid sequence of SEQ ID NO: 1, for example at least 7, 8, 9, 10, 11, 12, 13, 14, 15, 16, 17, 18, 19, 20, 30, 40, 50, 100, 150, 200, 210, 220, 230, 240, 250, 255, 260, 265, 270, 275, 280, 285, 286, 287, 288, 289 290, 291 or 292 contiguous amino acids of SEQ ID NO: 1.

Advantageously, the fragment comprises or consists of the inactivated RGD domain sequence of SEQ ID NO:2, namely:

```
        DISLAYGLRS          SEQ ID NO: 2
```

For example, the fragment may comprise or consist of an amino acid sequence according to any one SEQ ID NOs: 5 to 62.

In one particular embodiment, the polypeptide comprises or consists of the amino acid sequence of SEQ ID NO: 5.

```
   VDVPNGDISLAYGLR    SEQ ID NO: 5    ["FOL-004"]
```

In a further embodiment, the polypeptide comprises or consists of a variant of the amino acid sequence of SEQ ID NO: 1, or of a fragment thereof.

By "variant" we mean that the polypeptide does not share 100% amino acid sequence identity with SEQ ID NO: 1, i.e. one or more amino acids of SEQ ID NO: 1 must be mutated. For example, the polypeptide may comprise or consist of an amino acid sequence with at least 50% identity to the amino acid sequence of SEQ ID NO: 1, more preferably at least 60%, 70% or 80% or 85% or 90% identity to said sequence, and most preferably at least 95%, 96%, 97%, 98% or 99% identity to said amino acid sequence.

Percent identity can be determined by methods well known in the art, for example using the LALIGN program (Huang and Miller, *Adv. Appl. Math.* (1991) 12:337-357) at the Expasy facility site www.ch.embnet.org/software/LALIGNform.html using as parameters the global alignment option, scoring matrix BLOSUM62, opening gap penalty −14, extending gap penalty −4.

Alternatively, the percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

By "mutated" we mean that the amino acid at the specified position is altered compared to the amino acid in the polypeptide according to SEQ ID NO: 1. For example, an amino acid at a specified position may be deleted, substituted or may be the site of an insertion/addition of one or more amino acids. It will be appreciated by persons skilled in the art that the substitutions may be conservative or non-conservative.

Alternatively, or in addition, the amino acid at a specified position may be chemically modified (derivatised); see below.

In one embodiment, the variant polypeptide comprises or consists of an amino acid sequence of SEQ ID NO: 1, or a fragment thereof, in which one or more amino acids is conservatively substituted. By "conservatively substituted" we mean a substitution of one amino acid with another with similar properties (size, hydrophobicity, etc), such that the function of the polypeptide is not significantly altered. Thus, by "conservative substitutions" is intended combinations such as Gly, Ala; Val, Ile, Leu; Asp, Glu; Asn, Gln; Ser, Thr; Lys, Arg; and Phe, Tyr.

Advantageously, the variant comprises or consists of the inactivated RGD domain sequence of SEQ ID NO:2, namely:

```
        DISLAYGLRS          SEQ ID NO: 2
```

The variant polypeptide may also comprise one or more additional amino acids, inserted at the N- and/or C-terminus and/or internally within the amino acid sequence of SEQ ID NO:1. For example, the polypeptide may comprise or consist of at least 2, 3, 4, 5, 6, 7, 8, 9, 10, 15 or 20 additional amino acids at the N- and/or C-terminus and/or internally.

Advantageously, the variant polypeptide is non-naturally occurring.

In one preferred embodiment, the modified osteopontin polypeptide is a species homologue of the amino acid sequence of SEQ ID NO:1.

Thus, the polypeptide may comprise or consist of the amino acid sequence of a modified human osteopontin protein, or fragment thereof, in which an RGD domain is inactivated. Suitable human osteopontin protein sequences are well known in the art, for example see Database Accession Nos. AAA59974.1, AAC28619.1, AAA86886.1.

For example, the modified osteopontin polypeptide may comprise or consist of the amino acid sequence of SEQ ID NO:3 (in which the region encompassing the inactivated RGD domain is underlined)

```
                                        SEQ ID NO: 3
MRIAVICFCLLGITCAIPVKQADSGSSEEKQLYNKYPDAVATWLNP

DPSQKQNLLAPQTLPSKSNESHDHMDDMDDEDDDDHVDSQDSI

DSNDSDDVDDTDDSHQSDESHHSDESDELVTDFPTDLPATEVFT

PVVPTVDTYDGDISVVYGLRSKSKKFRRPDIQYPDATDEDITSHME

SEELNGAYKAIPVAQDLNAPSDWDSRGKDSYETSQLDDQSAETH

SHKQSRLYKRKANDESNEHSDVIDSQELSKVSREFHSHEFHSHED

MLVVDPKSKEEDKHLKFRISHELDSASSEVN
``` or a fragment, variant, derivative or fusion thereof (or a fusion of said fragment, variant or derivative) which retains the hair growth stimulatory activity of the amino acid sequence of SEQ ID NO:3.

Advantageously, the fragment or variant comprises or consists of the inactivated RGD domain sequence of SEQ ID NO:4, namely:

```
         DISVVYGLRS        SEQ ID NO: 4
```

For example, the fragment or variant may comprise or consist of an amino acid sequence according to any one SEQ ID NOs: 63 to 120 (as detailed below).

In one particular embodiment, the polypeptide comprises or consists of the amino acid sequence of SEQ ID NO: 63.

```
   VDTYDGDISVVYGLR    SEQ ID NO: 63    ["FOL-005"]
```

In a further embodiment, the modified osteopontin polypeptide comprises or consists of a derivative of the amino acid sequence of SEQ ID NO: 1 or 3, or of a fragment, variant or fusion thereof.

Advantageously, the derivative comprises the inactivated RGD domain sequence of SEQ ID NO:3 or 4.

For example, the polypeptide may comprise or consist of a derivative of the amino acid sequence of SEQ ID NO: 5 or 63

Chemical derivatives of one or more amino acids may be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

It will be further appreciated by persons skilled in the art that peptidomimetic compounds may also be useful, which mimic the conformation and desirable features of the modified osteopontin polypeptides detailed above. Thus, by 'polypeptide' we include peptidomimetic compounds which have the hair growth stimulatory activity of the polypeptide of SEQ ID NO: 1.

For example, the polypeptides of the invention include not only molecules in which amino acid residues are joined by peptide (—CO—NH—) linkages but also molecules in which the peptide bond is reversed. Such retro-inverso peptidomimetics may be made using methods known in the art, for example such as those described in Meziere et al. (1997) *J. Immunol.* 159, 3230-3237, which is incorporated herein by reference. This approach involves making pseudopeptides containing changes involving the backbone, and not the orientation of side chains. Retro-inverse peptides, which contain NH—CO bonds instead of CO—NH peptide bonds, are much more resistant to proteolysis. Alternatively, the polypeptide of the invention may be a peptidomimetic compound wherein one or more of the amino acid residues are linked by a -y($CH_2NH$)— bond in place of the conventional amide linkage.

In a further alternative, the peptide bond may be dispensed with altogether provided that an appropriate linker moiety which retains the spacing between the carbon atoms of the amino acid residues is used; it may be advantageous for the linker moiety to have substantially the same charge distribution and substantially the same planarity as a peptide bond.

It will be appreciated that the polypeptide may conveniently be blocked at its N— or C— terminus so as to help reduce susceptibility to exoproteolytic digestion.

A variety of uncoded or modified amino acids such as D-amino acids and N-methyl amino acids have also been used to modify mammalian polypeptides. In addition, a presumed bioactive conformation may be stabilised by a covalent modification, such as cyclisation or by incorporation of lactam or other types of bridges, for example see Veber et al., 1978, *Proc. Natl. Acad. Sci. USA* 75:2636 and Thursell et al., 1983, *Biochem. Biophys. Res. Comm.* 111:166, which are incorporated herein by reference.

A common theme among many of the synthetic strategies has been the introduction of some cyclic moiety into a peptide-based framework. The cyclic moiety restricts the conformational space of the peptide structure and this frequently results in an increased specificity of the peptide for a particular biological receptor. An added advantage of this strategy is that the introduction of a cyclic moiety into a peptide may also result in the peptide having a diminished sensitivity to cellular peptidases.

Thus, exemplary polypeptides of the invention comprise terminal cysteine amino acids. Such a polypeptide may exist in a heterodetic cyclic form by disulphide bond formation of the mercaptide groups in the terminal cysteine amino acids or in a homodetic form by amide peptide bond formation between the terminal amino acids. As indicated above, cyclising small peptides through disulphide or amide bonds between the N— and C— terminal region cysteines may circumvent problems of specificity and half-life sometime observed with linear peptides, by decreasing proteolysis and also increasing the rigidity of the structure, which may yield higher specificity compounds. Polypeptides cyclised by disulphide bonds have free amino and carboxy-termini which still may be susceptible to proteolytic degradation, while peptides cyclised by formation of an amide bond between the N-terminal amine and C-terminal carboxyl and hence no longer contain free amino or carboxy termini. Thus, the peptides of the present invention can be linked either by a C—N linkage or a disulphide linkage.

The present invention is not limited in any way by the method of cyclisation of peptides, but encompasses peptides whose cyclic structure may be achieved by any suitable it) method of synthesis. Thus, heterodetic linkages may include, but are not limited to formation via disulphide, alkylene or sulphide bridges. Methods of synthesis of cyclic homodetic peptides and cyclic heterodetic peptides, including disulphide, sulphide and alkylene bridges, are disclosed in U.S. Pat. No. 5,643,872, which is incorporated herein by reference. Other examples of cyclisation methods includes cyclization through click chemistry, epoxides, aldehyde-amine reactions, as well as and the methods disclosed in U.S. Pat. No. 6,008,058, which is incorporated herein by reference.

Such terminal modifications are useful, as is well known, to reduce susceptibility by proteinase digestion and therefore to prolong the half-life of the peptides in solutions, particularly in biological fluids where proteases may be present. Polypeptide cyclisation is also a useful modification because of the stable structures formed by cyclisation and in view of the biological activities observed for cyclic peptides.

Thus, in one embodiment the polypeptide of the first aspect of the invention is cyclic.

However, in an alternative embodiment, the polypeptide is linear.

In one preferred embodiment, however, the modified osteopontin polypeptide comprises one or more amino acids modified or derivatised by PEGylation, amidation, esterification, acylation, acetylation and/or alkylation.

Persons skilled in the art will appreciate that the modified osteopontin polypeptide may be glycosylated at one or more amino acids. For example, the polypeptide may retain one or more of the glycosylation sites of the corresponding ('parent') osteopontin protein, to which may be attached a carbohydrate group.

In a further embodiment, the modified osteopontin polypeptide comprises or consists of a fusion of the amino acid sequence of SEQ ID NO: 1 or 3, or of a fragment or variant thereof.

For example, the polypeptide may comprise a fusion of the amino acid sequence of SEQ ID NO: 5 or 63

By 'fusion' of a polypeptide we include an amino acid sequence corresponding to SEQ ID NO: 1 or 3 (or a fragment or variant thereof) fused to any other polypeptide. For example, the said polypeptide may be fused to a polypeptide such as glutathione-S-transferase (GST) or protein A in order to facilitate purification of said polypeptide. Examples of such fusions are well known to those skilled in the art. Similarly, the said polypeptide may be fused to an oligo-histidine tag such as His6 or to an epitope recognised by an antibody such as the well-known Myc tag epitope. Fusions to any variant or derivative of said polypeptide are also included in the scope of the invention.

The fusion may comprise a further portion which confers a desirable feature on the said polypeptide of the invention; for example, the portion may be useful in augmenting or prolonging the hair growth stimulatory effect. For example, in one embodiment the fusion comprises human serum albumin or similar protein (as disclosed in US 2009/0005312, the disclosures of which are incorporated herein by reference).

Alternatively, the fused portion may be a lipophilic molecule or polypeptide domain that is capable of promoting cellular uptake of the polypeptide, as known to those skilled in the art.

In a further embodiment, the modified osteopontin polypeptide comprises or consists of tandem repeats of an amino acid sequence. For example, the polypeptide may comprise or consist of tandem repeats of SEQ ID NO: 2 and/or 4 (or combinations thereof), which may be directly adjacent each other or separated by one or more intervening amino acids.

Alternatively, the polypeptide may comprise or consist of tandem repeats of the amino acid sequence of SEQ ID NO: 5 or 63.

In one preferred embodiment, however, the modified osteopontin polypeptide simply comprises or consists of the amino acid sequence of SEQ ID NO: 1 or 3. For example, the polypeptide may consist of the polypeptide according to SEQ ID NO: 1 or 3.

In a further preferred embodiment, the modified osteopontin polypeptide simply comprises or consists of the amino acid sequence of SEQ ID NO: 5 or 63. For example, the polypeptide may consist of the polypeptide according to SEQ ID NO: 5 or 63.

Modified osteopontin polypeptides suitable for use in the compositions of the invention may be made by in vitro cell-based expression methods well known to persons skilled in the art (for example, see Sambrook & Russell, 2000, *Molecular Cloning, A Laboratory Manual*, Third Edition, Cold Spring Harbor, N.Y., which is incorporated herein by reference). The choice of expression vector and host cell to be used may depend on a number of factors. For example, if the modified osteopontin polypeptide is to be glycosylated, a mammalian expression system will be required.

Suitable expression vectors and host cells are commercially available from many sources.

Alternatively, the modified osteopontin polypeptides may be synthesised by known means, such as liquid phase and solid phase synthesis (for example, t-Boc solid-phase peptide synthesis and BOP-SPPS).

It will be appreciated by persons skilled in the art that the present invention also includes pharmaceutically and/or cosmetically acceptable acid or base addition salts of the above described modified osteopontin polypeptides. The acids which are used to prepare the pharmaceutically and/or cosmetically acceptable acid addition salts of the aforementioned base compounds useful in this invention are those which form non-toxic acid addition salts, i.e. salts containing pharmaceutically and/or cosmetically acceptable anions, such as the hydrochloride, hydrobromide, hydroiodide, nitrate, sulphate, bisulphate, phosphate, acid phosphate, acetate, lactate, citrate, acid citrate, tartrate, bitartrate, succinate, maleate, fumarate, gluconate, saccharate, benzoate, methanesulphonate, ethanesulphonate, benzenesulphonate, p-toluenesulphonate and pamoate [i.e. 1,1'-methylene-bis-(2-hydroxy-3 naphthoate)] salts, among others.

Pharmaceutically and/or cosmetically acceptable base addition salts may also be used to produce pharmaceutically and/or cosmetically acceptable salt forms of the modified osteopontin polypeptides. The chemical bases that may be used as reagents to prepare pharmaceutically and/or cosmetically acceptable base salts of the present compounds that are acidic in nature are those that form non-toxic base salts with such compounds. Such non-toxic base salts include, but are not limited to those derived from such pharmaceutically and/or cosmetically acceptable cations such as alkali metal cations (e.g. potassium and sodium) and alkaline earth metal cations (e.g. calcium and magnesium), ammonium or water-soluble amine addition salts such as N-methylglucamine-(meglumine), and the lower alkanolammonium and other base salts of pharmaceutically acceptable organic amines, among others.

It will be further appreciated that the modified osteopontin polypeptides of the invention may be lyophilised for storage and reconstituted in a suitable carrier prior to use. Any suitable lyophilisation method (e.g. spray drying, cake drying) and/or reconstitution techniques can be employed. It will be appreciated by those skilled in the art that lyophilisation and reconstitution can lead to varying degrees of activity loss and that use levels may have to be adjusted upward to compensate. Preferably, the lyophilised (freeze dried) polypeptide loses no more than about 20%, or no more than about 25%, or no more than about 30%, or no more than about 35%, or no more than about 40%, or no more than about 45%, or no more than about 50% of its activity (prior to lyophilisation) when rehydrated.

The modified osteopontin polypeptides are provided in the form of a composition comprising the polypeptide and a pharmaceutically acceptable and/or cosmetically acceptable excipient, carrier or diluent, selected with regard to the intended route of administration and standard pharmaceutical or cosmetic practice (for example, see *Remington: The Science and Practice of Pharmacy*, 19$^{th}$ edition, 1995, Ed. Alfonso Gennaro, Mack Publishing Company, Pennsylvania, USA, which is incorporated herein by reference).

By "pharmaceutically acceptable" is included that the formulation is sterile and pyrogen free. Suitable pharmaceutical carriers are well known in the art of pharmacy. The carrier(s) must be "acceptable" in the sense of being compatible with the compound of the invention and not deleterious to the recipients thereof. Typically, the carriers will be water or saline which will be sterile and pyrogen free; however, other acceptable carriers may be used. Thus, "pharmaceutically acceptable carrier" and "pharmaceutically acceptable excipient" includes any compound(s) used in forming a part of the formulation that is intended to act merely as a carrier, i.e., not intended to have biological activity itself. The pharmaceutically acceptable carrier or excipient is generally safe, non-toxic, and neither biologically nor otherwise undesirable. A pharmaceutically acceptable carrier or excipient as used herein includes both one and more than one such carrier or excipient.

Likewise, the term "cosmetically acceptable" is used to denote formulations suitable for use as cosmetic products. Suitable cosmetic carriers are well known in the art, such as those commonly used in shampoos, lotions, creams and other such products.

The excipient may be one or more of carbohydrates, polymers, lipids and minerals. Examples of carbohydrates include lactose, sucrose, mannitol, and cyclodextrines, which are added to the composition, e.g., for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain lenght and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The term "diluent" is intended to mean an aqueous or non-aqueous solution with the purpose of diluting the peptide in the pharmaceutical preparation. The diluent may be one or more of saline, water, polyethylene glycol, propylene glycol, ethanol or oils (such as safflower oil, corn oil, peanut oil, cottonseed oil or sesame oil).

The diluent may also function as a buffer. The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

Optionally, the composition may comprise an adjuvant. The term "adjuvant" is intended to mean any compound added to the formulation to increase the biological effect of the peptide. The adjuvant may be one or more of zinc, copper or silver salts with different anions, for example, but not limited to fluoride, chloride, bromide, iodide, tiocyanate, sulfite, hydroxide, phosphate, carbonate, lactate, glycolate, citrate, borate, tartrate, and acetates of different acyl composition.

The pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly (carprolactone) (PCL), and polyanhydrides have been widely used as biodegradable polymers in the production of microspheres. Preparations of such microspheres can be found in U.S. Pat. No. 5,851,451 and in EP0213303.

The pharmaceutical compositions of the invention may also be in the form of polymer gels, where polymers such as starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, The modified osteopontin polypeptides may be formulated at various concentrations, depending on the efficacy/toxicity of the particular polypeptide being used. Preferably, the composition comprises the modified osteopontin polypeptide at a concentration of between 1 nM and 1 M, for example between 0.1 µM and 1 mM, 1 µM and 100 µM, between 5 µM and 50 µM, between 10 µM and 50 µM, between 20 µM and 40 µM and optionally about 30 µM. For ex vivo and in vitro applications, compositions may comprise a lower concentration of a modified osteopontin polypeptide, for example between 0.0025 µM and 1 µM.

It will be appreciated by persons skilled in the art that the compositions of the invention may be administered by a variety of routes, for example topical, transdermal, parenteral or oral administration.

Advantageously, the compositions of the invention are suitable for topical administration or intracutaneous administration.

Thus, the compositions of the invention may be administered topically to the skin (e.g. scalp). For example, the composition may be provided in the form of an ointment containing the active polypeptide suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the polypeptide can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Optionally, the composition for topical administration may comprise a penetration enhancer (for example, as described in Osborne & Henke, 1997, *Pharmaceutical Technology*, November: 58-82 and Pathan & Setty, 2009, *Tropical Journal of Pharmaceutical Research* 8 (2): 173-179, the disclosures of which are incorporated herein by reference).

Alternatively, the compositions of the invention may be administered parenterally, for example intracutaneously. Such compositions are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

It may be beneficial to use a sustained-release system, such as microsphere formulations, for delivering the modified osteopontin polypeptides.

Alternatively, compositions can be administered by a surgically implanted device that releases the active polypeptide directly to the required site (i.e. the epidermis).

The compositions of the invention may also be delivered by transdermal methodologies.

For example, electroporation therapy (EPT) and/or iontophoresis systems can be employed for the administration of proteins and polypeptides. In such methods, a device is used to deliver a pulsed electric field to cells, resulting in the increased permeability of the cell membranes to the drug and significant enhancement of intracellular drug delivery.

An alternative transdermal method, electroincorporation, utilises small particles of up to 30 microns in diameter on the surface of the skin experience electrical pulses identical or similar to those used in electroporation. The particles are driven through the stratum corneum and into deeper layers of the skin. The particles can be loaded or coated with drugs or genes or can simply act as "bullets" that generate pores in the skin through which the drugs can enter.

Additional transdermal methodologies have also been developed by PowderJect Pharmaceuticals (now owned by Novartis AG).

Suitable methods for administration of the polypeptides and compositions of the invention are well known in the art, for example, see *Therapeutic Protein and Peptide Formulation and Delivery*, Zahra Shahrokh et al. (Eds), 1997, American Chemical Society, ISBN13: 9780841235281.

A second aspect of the invention provides a polypeptide comprising or consisting of the amino acid sequence of SEQ ID NO: 63 or a fragment, variant, derivative or fusion thereof (or a fusion of said fragment, variant or derivative) which retains a hair growth stimulatory activity of the amino acid sequence of SEQ ID NO: 63.

In one embodiment, the polypeptide is isolated (e.g. outside the mammalian body).

The terms "fragment", "variant", "derivative" or "fusion" are as defined above in relation to the first aspect of the invention.

In a related aspect, the polypeptide is a fragment of human osteopontin comprising an RGD domain which is inactivated (by substitution or deletion of one or more of the amino acids of the RGD domain and/or by addition of one or more amino acids within the RGD domain). For example, the three amino acids of the "R-G-D" domain of the wildtype human osteopontin protein may be replaced by two amino acids, "D-I". Preferably, the fragment is between five and thirty amino acids in length, for example between ten and twenty amino acids in length.

For example, the polypeptide may comprise or consist of an amino acid sequence of any one of SEQ ID NOs: 5 to 62, or fragment, variant, derivative or fusion thereof.

Preferred 15-amino Acid Peptides

| | | |
|---|---|---|
| VDVPNG<u>DISLAYGLR</u> | ["FOL-004"] | SEQ ID NO: 5 |
| DVPNG<u>DISLAYGLRS</u> | | SEQ ID NO: 6 |

Preferred 14-amino Acid Peptides:

| | |
|---|---|
| VDVPNG<u>DISLAYGL</u> | SEQ ID NO: 7 |
| DVPNG<u>DISLAYGLR</u> | SEQ ID NO: 8 |
| VPNG<u>DISLAYGLRS</u> | SEQ ID NO: 9 |

Preferred 13-amino Acid Peptides:

| | |
|---|---|
| VDVPNG<u>DISLAYG</u> | SEQ ID NO: 10 |
| DVPNG<u>DISLAYGL</u> | SEQ ID NO: 11 |
| VPNG<u>DISLAYGLR</u> | SEQ ID NO: 12 |
| PNG<u>DISLAYGLRS</u> | SEQ ID NO: 13 |

Preferred 12-amino Acid Peptides:

| | |
|---|---|
| VDVPNG<u>DISLAY</u> | SEQ ID NO: 14 |
| DVPNG<u>DISLAYG</u> | SEQ ID NO: 15 |
| VPNG<u>DISLAYGL</u> | SEQ ID NO: 16 |
| PNG<u>DISLAYGLR</u> | SEQ ID NO: 17 |
| NG<u>DISLAYGLRS</u> | SEQ ID NO: 18 |

Preferred 11-amino Acid Peptides:

| | |
|---|---|
| VDVPNG<u>DISLA</u> | SEQ ID NO: 19 |
| DVPNG<u>DISLAY</u> | SEQ ID NO: 20 |

-continued

```
VPNGDISLAYG       SEQ ID NO: 21

PNGDISLAYGL       SEQ ID NO: 22

NGDISLAYGLR       SEQ ID NO: 23

GDISLAYGLRS       SEQ ID NO: 24
```

Preferred 10-amino acid peptides:

```
VDVPNGDISL        SEQ ID NO: 25

DVPNGDISLA        SEQ ID NO: 26

VPNGDISLAY        SEQ ID NO: 27

PNGDISLAYG        SEQ ID NO: 28

NGDISLAYGL        SEQ ID NO: 29

GDISLAYGLR        SEQ ID NO: 30

DISLAYGLRS        SEQ ID NO: 31
```

Preferred 9-amino Acid Peptides:

```
VDVPNGDIS         SEQ ID NO: 32

DVPNGDISL         SEQ ID NO: 33

VPNGDISLA         SEQ ID NO: 34

PNGDISLAY         SEQ ID NO: 35

NGDISLAYG         SEQ ID NO: 36

GDISLAYGL         SEQ ID NO: 37

DISLAYGLR         SEQ ID NO: 38

ISLAYGLRS         SEQ ID NO: 39
```

Preferred 8-amino Acid Peptides:

```
VDVPNGDI          SEQ ID NO: 40

DVPNGDIS          SEQ ID NO: 41

VPNGDISL          SEQ ID NO: 42

PNGDISLA          SEQ ID NO: 43

NGDISLAY          SEQ ID NO: 44

GDISLAYG          SEQ ID NO: 45

DISLAYGL          SEQ ID NO: 46

ISLAYGLR          SEQ ID NO: 47
```

Preferred 7-amino Acid Peptides:

```
VDVPNGD           SEQ ID NO: 48

DVPNGDI           SEQ ID NO: 49

VPNGDIS           SEQ ID NO: 50

PNGDISL           SEQ ID NO: 51

NGDISLA           SEQ ID NO: 52

GDISLAY           SEQ ID NO: 53

DISLAYG           SEQ ID NO: 54

ISLAYGL           SEQ ID NO: 55
```

Preferred 6-amino Acid Peptides:

```
DVPNGD            SEQ ID NO: 56

VPNGDI            SEQ ID NO: 57

PNGDIS            SEQ ID NO: 58

NGDISL            SEQ ID NO: 59

GDISLA            SEQ ID NO: 60

DISLAY            SEQ ID NO: 61

ISLAYG            SEQ ID NO: 62
```

In a preferred embodiment, the polypeptide comprises or consists of an amino acid sequence of SEQ ID NO: 5.

In an alternative embodiment, the polypeptide comprises or consists of a variant of an amino acid sequence of SEQ ID NO: 5.

For example, the polypeptide may comprise or consist of an amino acid sequence of any one of SEQ ID NOs: 63 to 120, or a fragment, variant, derivative or fusion thereof.

Preferred 15-amino Acid Peptides:

```
VDTYDGDISVVYGLR   ["FOL-005"]     SEQ ID NO: 63

VDTYDGDISVVYGLS                   SEQ ID NO: 64
```

Preferred 14-amino Acid Peptides:

```
VDTYDGDISVVYGL    SEQ ID NO: 65

DTYDGDISVVYGLR    SEQ ID NO: 66

TYDGDISVVYGLRS    SEQ ID NO: 67
```

Preferred 13-amino Acid Peptides:

```
VDTYDGDISVVYG     SEQ ID NO: 68

DTYDGDISVVYGL     SEQ ID NO: 69

TYDGDISVVYGLR     SEQ ID NO: 70

YDGDISVVYGLRS     SEQ ID NO: 71
```

Preferred 12-amino acid peptides:

```
VDTYDGDISVVY      SEQ ID NO: 72

DTYDGDISVVYG      SEQ ID NO: 73

TYDGDISVVYGL      SEQ ID NO: 74

YDGDISVVYGLR      SEQ ID NO: 75

DGDISVVYGLRS      SEQ ID NO: 76
```

Preferred 11-amino Acid Peptides:

```
VDTYDGDISVV       SEQ ID NO: 77

DTYDGDISVVY       SEQ ID NO: 78
```

-continued

| | |
|---|---|
| TYDG<u>DISVVYG</u> | SEQ ID NO: 79 |
| YDG<u>DISVVYGL</u> | SEQ ID NO: 80 |
| DG<u>DISVVYGLR</u> | SEQ ID NO: 81 |
| G<u>DISVVYGLRS</u> | SEQ ID NO: 82 |

Preferred 10-amino Acid Peptides:

| | |
|---|---|
| VDTYDG<u>DISV</u> | SEQ ID NO: 83 |
| DTYDG<u>DISVV</u> | SEQ ID NO: 84 |
| TYDG<u>DISVVY</u> | SEQ ID NO: 85 |
| YDG<u>DISVVYG</u> | SEQ ID NO: 86 |
| DG<u>DISVVYGL</u> | SEQ ID NO: 87 |
| G<u>DISVVYGLR</u> | SEQ ID NO: 88 |
| <u>DISVVYGLRS</u> | SEQ ID NO: 89 |

Preferred 9-amino Acid Peptides:

| | |
|---|---|
| VDTYDG<u>DIS</u> | SEQ ID NO: 90 |
| DTYDG<u>DISV</u> | SEQ ID NO: 91 |
| TYDG<u>DISVV</u> | SEQ ID NO: 92 |
| YDG<u>DISVVY</u> | SEQ ID NO: 93 |
| DG<u>DISVVYG</u> | SEQ ID NO: 94 |
| G<u>DISVVYGL</u> | SEQ ID NO: 95 |
| <u>DISVVYGLR</u> | SEQ ID NO: 96 |
| <u>ISVVYGLRS</u> | SEQ ID NO: 97 |

Preferred 8-amino Acid Peptides:

| | |
|---|---|
| VDTYDG<u>DI</u> | SEQ ID NO: 98 |
| DTYDG<u>DIS</u> | SEQ ID NO: 99 |
| TYDG<u>DISV</u> | SEQ ID NO: 100 |
| YDG<u>DISVV</u> | SEQ ID NO: 101 |
| DG<u>DISVVY</u> | SEQ ID NO: 102 |
| G<u>DISVVYG</u> | SEQ ID NO: 103 |
| <u>DISVVYGL</u> | SEQ ID NO: 104 |
| <u>ISVVYGLR</u> | SEQ ID NO: 105 |

Preferred 7-amino Acid Peptides:

| | |
|---|---|
| VDTYDG<u>D</u> | SEQ ID NO: 106 |
| DTYDG<u>DI</u> | SEQ ID NO: 107 |
| TYDG<u>DIS</u> | SEQ ID NO: 108 |
| YDG<u>DISV</u> | SEQ ID NO: 109 |
| DG<u>DISVV</u> | SEQ ID NO: 110 |
| G<u>DISVVY</u> | SEQ ID NO: 111 |
| <u>DISVVYG</u> | SEQ ID NO: 112 |
| <u>ISVVYGL</u> | SEQ ID NO: 113 |

Preferred 6-amino Acid Peptides:

| | |
|---|---|
| DTYDG<u>D</u> | SEQ ID NO: 114 |
| TYDG<u>DI</u> | SEQ ID NO: 115 |
| YDG<u>DIS</u> | SEQ ID NO: 116 |
| DG<u>DISV</u> | SEQ ID NO: 117 |
| G<u>DISVV</u> | SEQ ID NO: 118 |
| <u>DISVVY</u> | SEQ ID NO: 119 |
| <u>ISVVYG</u> | SEQ ID NO: 120 |

In a preferred embodiment, the polypeptide comprises or consists of an amino acid sequence of SEQ ID NO: 63.

The polypeptides of the invention may be for medical use in the treatment or prevention of a disease or condition associated with hair loss (as described in detail below).

The invention further provides the use of a polypeptide of the invention for stimulating hair growth in a mammal, wherein the use is cosmetic or commercial (as described in detail below).

A third aspect of the invention provides compositions according to the first aspect of the invention for use in stimulating hair growth in a mammal.

Thus, the compositions may be for use in stimulating existing hair follicles and/or inducing the growth of new hair follicles (or stem cells for producing the same).

In one embodiment, the composition is for use in the treatment or prevention of a disease or condition associated with hair loss, such as alopecia.

Alopecia is typically associated with the loss of anagen hairs. However, it will be appreciated that the compositions of the invention may also be used for treatment of conditions associated with the loss of telogen hairs.

In one embodiment, the alopecia is selected from the group consisting of:
(a) androgenic alopecia (also known as androgenetic alopecia, alopecia androgenetica, male pattern baldness or female pattern baldness);
(b) traction alopecia;
(c) anagen effluvium;
(d) telogen effluvium;
(e) alopecia areata;
(f) alopecia totalis;
(g) alopecia universalis;
(h) alopecia barbae;
(i) alopecia mucinosa;
(j) alopecia neoplastica;
(k) cicatricial alopecia; and
(l) scarring alopecia.

For example, the alopecia may be androgenic alopecia.

Alternatively, the alopecia may be anagen effluvium. This condition, resulting from the early entry of hairs into the telogen phase, may be due to a variety of causes, including eating disorders, fever, childbirth, chronic illness, major surgery, anemia, severe emotional disorders, crash diets, hypothyroidism, and drugs.

Thus, in one embodiment, the hair loss is induced by radiotherapy and/or chemotherapy agents. For example, hair loss is a common and distressing side effect of treatment with chemotherapeutic drugs such as cisplatin, etoposide and paclitaxel.

Conveniently, the mammal is a human.

A related, fourth aspect of the invention provides the use of a modified osteopontin polypeptide as defined above in relation to the first aspect of the invention in the preparation of a medicament for stimulating hair growth in a mammal.

Thus, the medicament may be for stimulating existing hair follicles and/or inducing the growth of new hair follicles (or stem cells for producing the same).

In one embodiment, the medicament is for the treatment or prevention of a disease or condition associated with hair loss, such as alopecia (e.g. associated with the loss of anagen hairs).

In one embodiment, the alopecia is selected from the group consisting of:
(a) androgenic alopecia (also known as androgenetic alopecia, alopecia androgenetica, male pattern baldness or female pattern baldness);
(b) traction alopecia;
(c) anagen effluvium;
(d) telogen effluvium;
(e) alopecia areata;
(f) alopecia totalis;
(g) alopecia universalis;
(h) alopecia barbae;
(i) alopecia mucinosa;
(j) alopecia neoplastica;
(k) cicatricial alopecia; and
(l) scarring alopecia.

For example, the alopecia may be androgenic alopecia.

Alternatively, the alopecia may be anagen effluvium, e.g. induced by radiotherapy and/or chemotherapy (see above).

Conveniently, the mammal is a human.

A related, fifth aspect of the invention provides a method for stimulating hair growth in a mammal comprising administering an effective amount of a modified osteopontin polypeptide as defined above in relation to the first aspect of the invention.

Thus, the method may be for stimulating existing hair follicles and/or inducing the growth of new hair follicles (or stem cells for producing the same).

The polypeptide composition of the invention is administered to the patient in an effective amount. A 'therapeutically effective amount', or 'effective amount', or 'therapeutically effective', as used herein, refers to that amount which provides a stimulatory effect on hair growth. This is a predetermined quantity of active material calculated to produce the desired therapeutic effect. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

In one embodiment, the method is for the treatment or prevention of a disease or condition associated with hair loss, such as alopecia (e.g. associated with the loss of anagen hairs).

In one embodiment, the alopecia is selected from the group consisting of:

(a) androgenic alopecia (also known as androgenetic alopecia, alopecia androgenetica, male pattern baldness or female pattern baldness);
(b) traction alopecia;
(c) anagen effluvium;
(d) telogen effluvium;
(e) alopecia areata;
(f) alopecia totalis;
(g) alopecia universalis;
(h) alopecia barbae;
(i) alopecia mucinosa;
(j) alopecia neoplastica;
(k) cicatricial alopecia; and
(l) scarring alopecia.

For example, the alopecia may be androgenic alopecia.

Alternatively, the alopecia may be anagen effluvium, e.g. induced by radiotherapy and/or chemotherapy (see above).

Conveniently, the mammal is a human.

It will be appreciated by persons skilled in the art that the composition of the first aspect of the invention are not limited to medical uses but may also be used as cosmetic agents (in the sense that they do not provide any physical health improvement, as such, but merely provide an aesthetic benefit to the mammal).

Thus, a sixth aspect of the invention provides the use of a composition according to the first aspect of the invention for stimulating hair growth in a mammal, wherein the use is cosmetic.

Thus, the cosmetic composition may be for stimulating existing hair follicles and/or inducing the growth of new hair follicles (or stem cells for producing the same).

In one embodiment, the cosmetic composition is used for the treatment or prevention of baldness, which may be associated with a receding hairline and/or thinning hair.

Such compositions are not limited to use on the scalp, but may also be applied elsewhere on the body (including to the face to encourage the growth of a beard, eyelashes, eyebrows, etc.)

Conveniently, the mammal is a human.

It will be appreciated by persons skilled in the art that the compositions of the invention may be used on their own or in combination with other therapeutic or cosmetic agents. For example, the compositions of the invention may be used in a combination therapy with existing treatments to prevent loss of existing hair and/or to stimulate growth of new hair, for example potassium channel openers, such as minoxidil (Regaine®, Pharmacia Corp.) and diazoxide; 5-alpha-reductase inhibitors, such as finasteride (Propecia®, Merck & Co.); and the immunosuppressant cyclosporin A.

It will be further appreciated by skilled persons that the compositions of the invention may be used in vivo, ex vivo or in vitro.

Thus, in addition to being applied or administered directly to a mammal, the compositions may be used to stimulate hair growth ex vivo, for example in a skin explant prior to grafting of the skin on to the mammal.

Alternatively, the compositions may be used to grow hair follicles in vitro, e.g. in cell culture, which may then be transplanted to a patient.

Accordingly, a further aspect of the invention provides the use of a polypeptide according to the first aspect of the invention for stimulating hair growth in vitro or ex vivo.

In one embodiment, the polypeptide is used to stimulate the growth of hair follicles (or stem cell precursors of the same).

A still further aspect of the invention provides a method for making a composition according to the first aspect of the invention, the method comprising admixing a modified osteopontin polypeptide in which an RGD domain is inactivated with a pharmaceutically acceptable and/or cosmetically acceptable excipient, carrier or diluent.

BRIEF DESCRIPTION OF DRAWINGS

Preferred, non-limiting examples which embody certain aspects of the invention will now be described, with reference to the following figures.

EXAMPLE A

In vivo Study of Hair Growth Effect of Mutated Mouse Osteopontin in Mice

Materials and Methods
Creation and Production of Test Polypeptide

The modified osteopontin polypeptide sequence SEQ ID NO:1 was cloned into a pCEP4 expression vector by the use of XhoI and BamHI restriction enzyme sites. The pCEP4 expression vector contains an ampicillin resistance gene for expression in bacteria and a hygromycin resistance gene for expression in eukaryotic EBNA cells. The polypeptide containing vector were transformed into competent XL-10 bacteria cells, multiplied and isolated with Qiagen midi prep kit. Isolated vectors were then transfected into human EBNA cells by the use of Fugene transfection reagent according to manufacture protocol (Invitrogen).
Isolation of Test Polypeptide Medium from EBNA cell culture containing the produced polypeptide were collected after three to four days of culture. Polypeptides produced by pCEP4 plasmid contain an inserted His-tag, which is used to facilitate the isolation with Ni-sepharose gel chromatography (Invitrogen). Collected medium was diluted with binding buffer (20 mM sodium phosphate, 500 mM sodium chloride, pH 7.8), Ni-sepharose suspension was added before incubation on shaker overnight at 4° C. The Ni-sepharose gel was pelleted by centrifugation at 1000 g for seven minutes and poured into a BioRad disposable mini column. Unbound proteins were removed with binding buffer followed by washing buffer (20 mM sodium phosphate, 500 mM sodium chloride, pH 6.0). Polypeptides were eluted from the column with 500 mM imidazole.
General Study Design The study consisted of four experimental groups each containing five male wtC57BL/6N mice.

Figure 1:
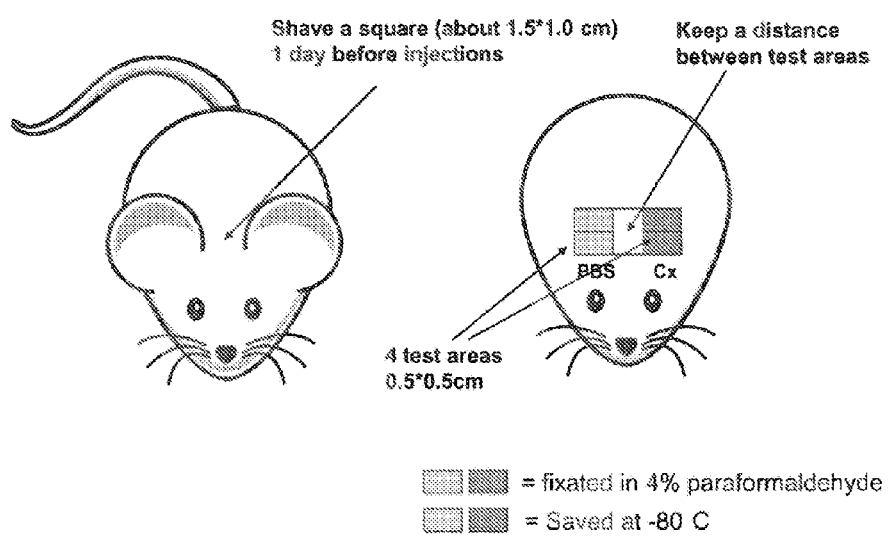
FIG. 1 shows a schematic representation of the sampling area of skin on the mice.

On day −1 the necks of all participating mice were shaved carefully in squares of approx. 1.5×1.0 cm and small remaining hairpieces were removed. On the following day (day 0), each animal received four intracutaneous injections of 25 μl each at separate locations (each approx. 0.5×0.5 cm) within the shaved rectangle (see FIG. 1).

Each animal received two injections of 25 μl of a composition comprising an exemplary modified osteopontin polypeptide of SEQ ID NO:1 ("Test polypeptide" or "Cx", 60 nmol/I in PBS) and two negative control injections of 25 μl PBS (according to the scheme outlined in Table 1).

TABLE 1

Study Design

| Group | Intracutaneous Application | | |
|---|---|---|---|
| | Volume | Time schedule after application | Number of animals |
| 1 Test polypeptide + PBS | 25 μl | Necropsy after 24 h (day 1) | 5 |
| 2 Test polypeptide + PBS | 25 μl | Necropsy after 48 h (day 2) | 5 |
| 3 Test polypeptide + PBS | 25 μl | Necropsy after 96 h (day 4) | 5 |
| 4 Test polypeptide + PBS | 25 μl | Necropsy after 336 h (day 14) | 5 |

Animals from Treatment Groups 1 to 4 were sacrificed 24 h (Group 1), 48 h (Group 2), 96 h (Group 3) and 336 h (14 days, Group 4) after compound application, respectively.

In all cases, the marked skin areas in the neck were removed and processed as follows: One of the polypeptide-treated skin samples and one of the PBS-treated control skin samples were fixed in 4% paraformaldehyde and subsequently embedded in paraffin. The two other skin samples (polypeptide-treated and PBS-treated) were snap-frozen in liquid nitrogen and stored appropriately at −80° C.

A Hematoxylin-staining of the paraffin-embedded sections was performed.
Animals
Rationale Accepted test system for the purpose of the study
Strain male wtC57BL/6N
Source Charles River GmbH
  Sandhofer Weg 7
  D 97633 Sulzfeld
Total number of animals 20
Age at delivery 5-6 weeks
Body weight and range approx. 30 g
(at acclimatisation)
Identification Labeling by ear mark
Acclimatisation February, 17 to Mar., 1 2011
Husbandry
Conditions Optimum hygienic conditions, air-conditioned with 10-15 air changes per hour, and continually monitored environment with target ranges for temperature 22±3° C. and for relative humidity 30-70%, 12 hours artificial fluorescent light/12 hours dark.
Accommodation max. 3 animals per cage Diet M-Zucht
 ssniff Spezialdiäten GmbH
 Ferdinand Gabriel Weg 16
 D-59494 Soest
Water Community tap water (autoclaved)
Test Polypeptide
 Identification Modified osteopontin polypeptide of SEQ ID NO:1
Storage conditions stored in Hepes buffer at 4° C.
Safety precautions prevent ingestion, inhaling, wear gloves and skin mask, wash with soap and water after skin contact; no special precautions
Sample preparation delivered stock solution was diluted 15× with PBS to obtain the 60 nM working solution before injection
Vehicle
 Identity PBS pH 7.4
Treatment
Route of administration: intracutaneously
Frequency of administration single application on day 0 Dose volume 25 µl
Observations
 The following parameters were recorded:
Viability/Mortality daily
Clinical signs daily
Protocol for Hematoxylin-Staining of Paraffin-Embedded Sections of Group 1
1. Xylen bath 5 min
2. Xylen bath 5 min
3. EtOH 100% bath 5 min
4. EtOH 95% bath 5 min
5. EtOH 70% bath 5 min
6. PBS bath 5 min
7. Hematoxylin bath about 20 sec (Harrys Hematoxylin)[a),b)]
8. Water bath 3 times 3 min
9. EtOH 70% bath 5 min
10. EtOH 95% bath 5 min
11. EtOH 100% bath 5 min
12. Xylen bath 5 min
13. Xylen bath 5 min
14. Mount slide using Permount and coveslip.
a) the time depends on the type of hematoxylin used, 20 sec to 10 min (which can be determined by the use of test slides)
b) filtrated before use
Results
 The effect of treatment with a modified osteopontin polypeptide (SEQ ID NO:1) on hair follicle density is summarised in Table 1(a) and (b) below.

TABLE 1(a)

| Polypeptide-treated animals | Number of hair follicles | Length of epidermis, mm |
|---|---|---|
| Polypeptide treated Slide 1 | | |
| area a1 | 18 | 0.90 |
| area a2 | 21 | 0.90 |
| area a3 | 25 | 0.95 |
| area b1 | 13 | 0.90 |
| area b2 | 21 | 0.90 |
| area b3 | 26 | 0.95 |
| Sum | 124 | 5.50 |
| Polypeptide treated Slide 2 | | |
| area a1 | 16 | 0.90 |
| area a2 | 18 | 0.90 |
| area a3 | 25 | 0.95 |
| area b1 | 14 | 0.90 |
| area b2 | 18 | 0.90 |
| area b3 | 19 | 0.95 |
| Sum | 110 | 5.50 |
| Polypeptide treated Slide 3 | | |
| area a1 | 18 | 0.90 |
| area a2 | 13 | 0.90 |
| area a3 | 19 | 0.95 |
| area b1 | 20 | 0.90 |
| area b2 | 17 | 0.90 |
| area b3 | 14 | 0.90 |
| Sum | 101 | 5.45 |
| Polypeptide treated Slide 4 | | |
| area a1 | 18 | 0.90 |
| area a2 | 17 | 0.90 |
| area a3 | 15 | 0.90 |
| area b1 | 18 | 0.90 |
| area b2 | 17 | 0.90 |
| area b3 | 13 | 0.90 |
| Sum | 98 | 5.40 |
| Polypeptide treated Slide 5 | | |
| area a1 | 13 | 0.90 |
| area a2 | 10 | 0.90 |
| area a3 | 21 | 0.90 |
| area b1 | 12 | 0.90 |
| area b2 | 10 | 0.90 |
| area b3 | 16 | 0.90 |
| Sum | 82 | 5.40 |
| Polypeptide treated Slide 6 | | |
| area a1 | 18 | 0.90 |
| area a2 | 10 | 0.90 |
| area a3 | 10 | 0.90 |
| area b1 | 18 | 0.90 |
| area b2 | 17 | 0.90 |
| area b3 | 10 | 0.90 |
| Sum | 83 | 5.40 |
| Polypeptide treated Slide 7 | | |
| Slide 34 | 124 | 5.50 |
| Slide 38 | 110 | 5.50 |
| Slide 42 | 101 | 5.45 |
| Slide 46 | 98 | 5.40 |
| Slide 50 | 82 | 5.40 |
| Slide 54 | 83 | 5.40 |
| Total | 598 | 32.65 |

TABLE 1(b)

| Control-treated animals | Number of hair follicles | Length of epidermis, mm |
|---|---|---|
| Control treated Slide 1 | | |
| area a1 | 9 | 0.90 |
| area a2 | 17 | 0.90 |
| area a3 | 7 | 0.90 |

TABLE 1(b)-continued

| | Control-treated animals | |
|---|---|---|
| | Number of hair follicles | Length of epidermis, mm |
| area b1 | 11 | 0.90 |
| area b2 | 14 | 0.95 |
| area b3 | 10 | 0.90 |
| Sum Control treated Slide 2 | 68 | 5.45 |
| area a1 | 12 | 0.90 |
| area a2 | 17 | 0.90 |
| area a3 | 7 | 0.90 |
| area b1 | 12 | 0.90 |
| area b2 | 13 | 0.90 |
| area b3 | 10 | 0.90 |
| Sum Control treated Slide 3 | 71 | 5.40 |
| area a1 | 8 | 0.90 |
| area a2 | 7 | 0.90 |
| area a3 | 11 | 0.90 |
| area b1 | 19 | 0.95 |
| area b2 | 8 | 0.90 |
| area b3 | 14 | 0.90 |
| Sum Control treated Slide 4 | 67 | 5.45 |
| area a1 | 21 | 0.90 |
| area a2 | 5 | 0.90 |
| area a3 | 2 | 0.90 |
| area b1 | 16 | 0.90 |
| area b2 | 11 | 0.90 |
| area b3 | 3 | 0.90 |
| Sum Control treated Slide 5 | 58 | 5.40 |
| area a1 | 13 | 0.90 |
| area a2 | 2 | 0.90 |
| area a3 | 9 | 0.90 |
| area b1 | 12 | 0.90 |
| area b2 | 7 | 0.90 |
| area b3 | 15 | 0.90 |
| Sum Control treated Slide 6 | 58 | 5.40 |
| area a1 | 7 | 0.90 |
| area a2 | 11 | 0.90 |
| area a3 | 10 | 0.90 |
| area b1 | 6 | 0.90 |
| area b2 | 8 | 0.90 |
| area b3 | 15 | 0.90 |
| Sum Control treated Slide 7 | 57 | 5.40 |
| Slide 18 | 68 | 5.45 |
| Slide 22 | 71 | 5.40 |
| Slide 26 | 67 | 5.45 |
| Slide 34 | 58 | 5.40 |
| Slide 38 | 58 | 5.40 |
| Slide 42 | 57 | 5.40 |
| Total | 379 | 32.50 |

A summary of the results is shown below in Table 2

TABLE 2

| | No. of follicles analysed | No. of follicles per mm |
|---|---|---|
| Treatment with SEQ ID NO: 1 | 356 | 18.3 |
| Control group | 356 | 11.7 |

Figure 2:
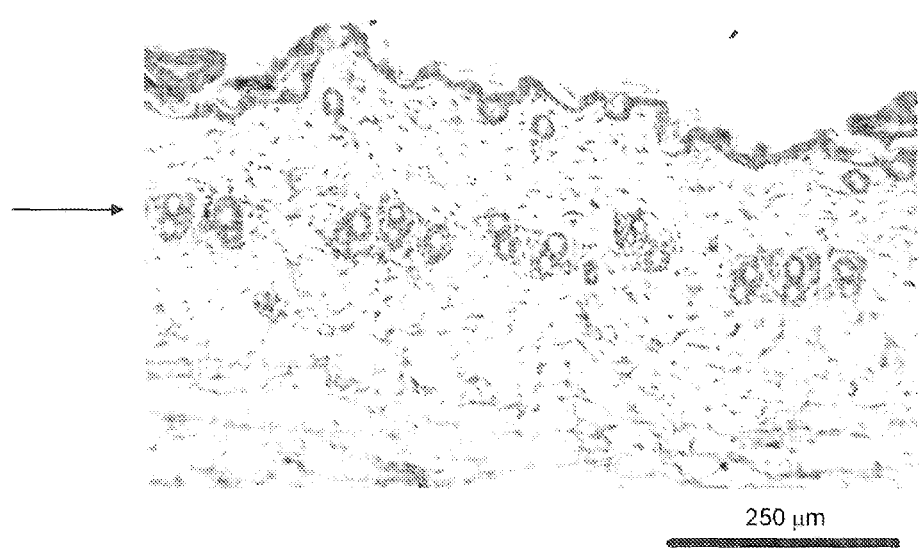
FIG. 2 is a representative photograph of a cross section of skin from a mouse 48 hours after being treated with a modified osteopontin polypeptide. Follicles within the epidermis are indicated by the arrow. The linear density of the follicles was 18.3 follicles per mm (598 follicles in 32.65 mm of epidermis).
Figure 3:
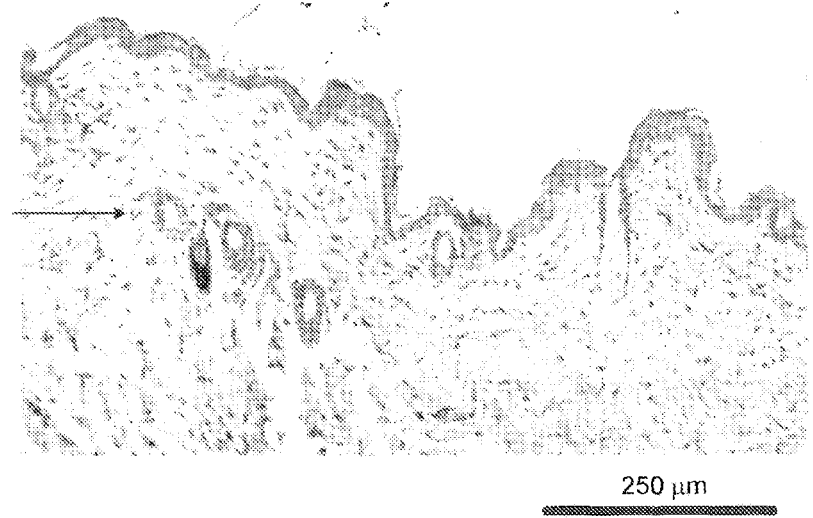
FIG. 3 is a representative photograph of a cross section of skin from a mouse 48 hours after being treated with a negative control composition. Follicles within the epidermis are indicated by the arrow. The linear density of the follicles was 11.7 follicles per mm (379 follicles in 32.50 mm of epidermis).
Figure 4A:
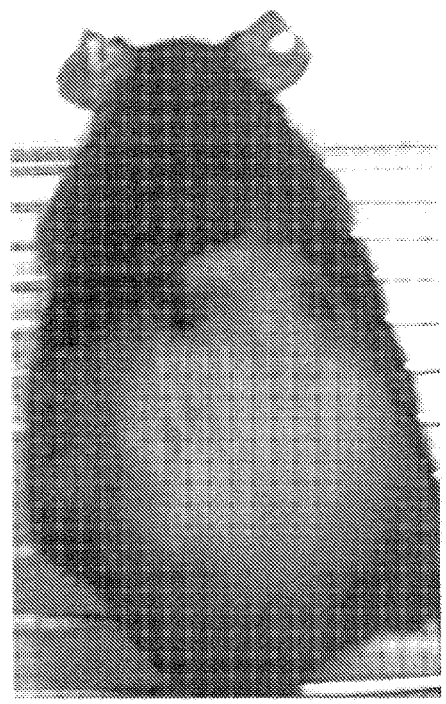
FIG. 4 shows representative photographs of (a) a control-treated animal on day 14 having a hair growth score of 0, (b) an animal treated with exemplary 'full length' polypeptide "Cx" (corresponding to SEQ ID NO: 1 but without the initial sixteen amino acid signal peptide, 60 nM) on day 14 having a hair growth score of 1.5 (c) an animal treated with exemplary short peptide "FOL-004" (SEQ ID NO: 5, 60 nM) on day 5 having a hair growth score of 2.5 and (d) an animal treated with exemplary short peptide "FOL-005" (SEQ ID NO: 5, 63 nM) on day 5 having a hair growth score of 2.0.
Figure 4B:
Figure 4C:
Figure 4D:

Representative tissue sections showing follicles in treated and control animals are shown in FIGS. 2 and 3.

By comparison, wildtype mouse osteopontin was observed to have no detectable effect on hair growth (data not shown).

Conclusions

The data show that treatment with the exemplary modified osteopontin polypeptide of SEQ ID NO: 1 increases the number of hair follicles/mm epidermis by about 60%.

These findings confirm the usefulness of the osteopontin-like polypeptides of the invention in stimulating hair growth.

EXAMPLE B

In vivo Study of Hair Growth Effect of SEQ ID NOS: 5 and 63 in Mice

Materials and Methods

Animals

Mice (C57BU6) were used at an age of 6 to 8 weeks.

Overview of Study Design

Selection of animals in telogen phase of hair growth.

Clipping of dorsal back of animals

Subcutaneous injection of test peptide/vehicle

Visual analysis: Percentage anagen induction; Mean hair growth score; Visual melanogenesis:

Histological analysis: Follicle count in subcutis; Morphometry for skin thickness.

Treatment Groups

Animals were assigned randomly to treatment groups (see Table 3)

TABLE 3

| Treatment | No. of animals | Dose | Volume |
|---|---|---|---|
| "Cx" | 5 | 60 nM | 25 µl |
| "FOL-004" (=SEQ ID NO: 5) | 5 | 60 nM | 25 µl |
| "FOL-005" (=SEQ ID NO: 63) | 5 | 60 nM | 25 µl |
| Vehicle control | 5 | — | 25 µl |

Animals were administered the specified treatment on Days 1, 5 and 9

Treatment were administered by subcutaneous injection into dorsal clipped skin

Scoring Criteria

The effect of the treatments was observed and scored daily according to the criteria in Table 4

TABLE 4

| Observation of dorsal skin | Hair growth score |
|---|---|
| No hair growth, pink skin | 0 |
| Skin colour changes from pink to gray without visible hair growth | 0.5 |
| Skin colour changes from pink to gray or black without visible hair growth, indicating the onset of anagen | 1 |
| Sparse hair growth | 1.5 |
| Diffuse short hair growth | 2 |
| Moderate hair growth | 2.5 |
| Dense, normal coat hair | 3 |

Results

The effect of the exemplary polypeptides of the invention on hair growth is shown in Table 5.

TABLE 5

| | Day | | | | | | | | | | | |
|---|---|---|---|---|---|---|---|---|---|---|---|---|
| Animal | 1 | 2 | 5 | 6 | 7 | 8 | 9 | 12 | 13 | 14 | 15 | 16 |
| (A) Vehicle (control) | | | | | | | | | | | | |
| 1 | 0 | 0 | 0 | 0 | 0 | 0 | 0 | 0 | 0 | 0 | NA | NA |
| 2 | 0 | 0 | 0 | 0 | 0 | 0 | 0 | 0 | 0 | 0 | NA | NA |
| 3 | 0 | 0 | 0 | 0 | 0 | 0 | 0 | 0 | 0 | 0 | NA | NA |
| 4 | 0 | 0 | 0 | 0 | 0 | 0 | 0 | 0 | 0 | 0 | NA | NA |
| 5 | 0 | 0 | 0 | 0 | 0 | 0 | 0 | 0.5 | 1 | 1 | NA | NA |
| Mean | 0.0 | 0.0 | 0.0 | 0.0 | 0.0 | 0.0 | 0.0 | 0.1 | 0.2 | 0.2 | — | — |
| (B) "Cx" (SEQ ID NO: 1 minus the initial 16 amino acid signal peptide) | | | | | | | | | | | | |
| 1 | 0 | 0 | 0 | 1 | 1.5 | 2 | 2.5 | 3 | 3 | 3 | NA | NA |
| 2 | 0 | 0 | 0 | 0.5 | 0.5 | 0.5 | 0.5 | 1 | 1 | 1 | NA | NA |
| 3 | 0 | 0 | 0 | 0.5 | 0.5 | 0.5 | 1 | 1.5 | 1.5 | 1.5 | NA | NA |
| 4 | 0 | 0 | 0 | 0.5 | 0.5 | 0.5 | 1 | 1.5 | 1.5 | 1.5 | NA | NA |
| 5 | 0 | 0 | 0 | 0 | 0 | 0 | 0.5 | 1 | 1.5 | 2 | NA | NA |
| Mean | 0.0 | 0.0 | 0.0 | 0.5 | 0.6 | 0.7 | 1.1 | 1.6 | 1.7 | 1.8 | — | — |
| (C) FOL-004 (SEQ ID NO: 5) | | | | | | | | | | | | |
| 1 | 0 | 0 | 0.5 | 1 | 1 | 1 | 1 | 1.5 | 1.5 | 1.5 | 2.5 | 3 |
| 2 | 0 | 0 | 2.5 | 2.5 | 3 | 3 | 3 | 3 | 3 | 3 | 3 | 3 |
| 3 | 0 | 0 | 2.5 | 2.5 | 2.5 | 3 | 3 | 3 | 3 | 3 | 3 | 3 |
| 4 | 0 | 0 | 1.5 | 2.5 | 3 | 3 | 3 | 3 | 3 | 3 | 3 | 3 |
| 5 | 0 | 0 | 1.5 | 2 | 2.5 | 2.5 | 3 | 3 | 3 | 3 | 3 | 3 |
| Mean | 0.0 | 0.0 | 1.7 | 2.1 | 2.4 | 2.5 | 2.6 | 2.7 | 2.7 | 2.7 | 2.9 | 3.0 |
| (D) FOL-005 (SEQ ID NO: 63) | | | | | | | | | | | | |
| 1 | 0 | 0 | 2 | 2.5 | 3 | 3 | 3 | 3 | 3 | 3 | 3 | 3 |
| 2 | 0 | 0 | 2 | 3 | 3 | 3 | 3 | 3 | 3 | 3 | 3 | 3 |
| 3 | 0 | 0 | 0.5 | 0.5 | 1 | 1 | 1.5 | 2.5 | 2.5 | 2.5 | 3 | 3 |
| 4 | 0 | 0 | 2 | 2.5 | 2.5 | 3 | 3 | 3 | 3 | 3 | 3 | 3 |
| 5 | 0 | 0 | 0 | 0 | 0 | 0.5 | 1 | 2 | 2.5 | 2.5 | 3 | 3 |
| Mean | 0.0 | 0.0 | 1.3 | 1.7 | 1.9 | 2.1 | 2.3 | 2.7 | 2.8 | 2.8 | 3.0 | 3.0 |

FIG. 4 shows representative photographs of (a) a control-treated animal on day 14 having a hair growth score of 0, (b) an animal treated with exemplary 'full length' polypeptide "Cx" (SEQ ID NO: 1, 60 nM) on day 14 having a hair growth score of 1.5 (c) an animal treated with exemplary short peptide "FOL-004" (SEQ ID NO: 5, 60 nM) on day 5 having a hair growth score of 2.5 and (d) an animal treated with exemplary short peptide "FOL-005" (SEQ ID NO: 5, 63 nM) on day 5 having a hair growth score of 2.0.

Figure 5:
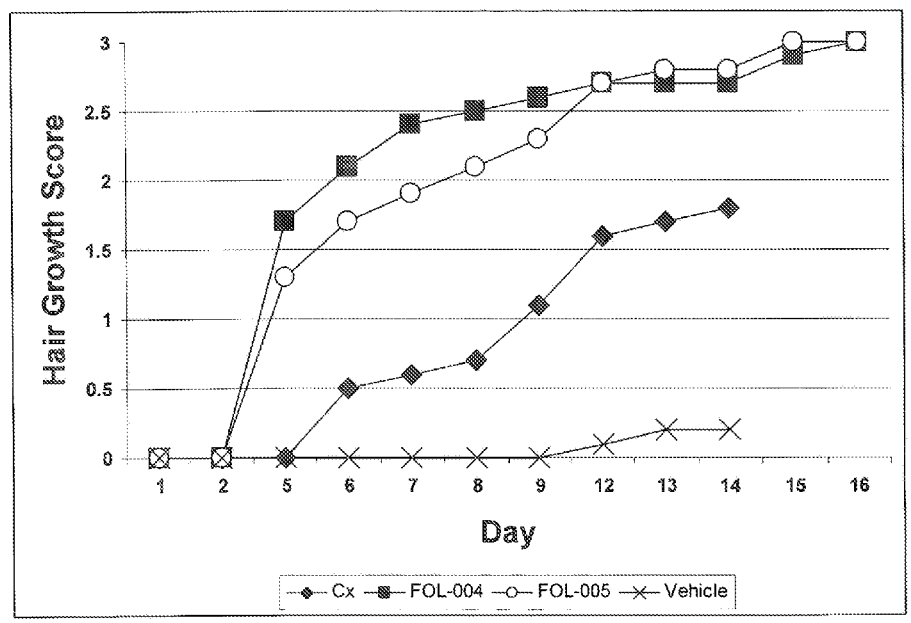
FIG. 5 shows the effect of exemplary 'full length' polypeptide "Cx" and polypeptides SEQ ID NOs: 5 and 63 of the invention on hair growth.

The results are summarised in FIG. 5.

Exemplary polypeptides FOL-004 (SEQ ID NO: 5) and FOL-005 (SEQ ID NO: 63) both induced rapid hair growth, which was evident from day 5 and maintained until the end of the assessment period (day 16).

A 'full length' polypeptide of the invention, ("Cx") also induced pronounced hair growth, albeit with a slower onset than the FOL-004 (SEQ ID NO: 5) or FOL-005 (SEQ ID NO: 63).

Animals treated with the vehicle control showed little sign of hair growth over the period of the experiment.

None of the polypeptides tested lead to any adverse effects in the animals (no body weight loss or any other discernible adverse symptom).

Conclusions

All mutated osteopontin polypeptides tested showed pronounced hair growth effects in vivo, with the shorter exemplary polypeptides FOL-004 (SEQ ID NO: 5) and FOL-005 (SEQ ID NO: 63) exhibiting a particular fast onset of action.

EXAMPLE C

In vivo Study of Hair Growth Effect in Mice of the Wildtype Osteopontin Fragment Equivalent to SEQ ID NO: 5

Materials and Methods

Animals, as described above in Example B, were treated as described in Table 6:

TABLE 6

| Treatment | No. of animals | Dose | Volume |
|---|---|---|---|
| "FOL-001"* (=SEQ ID NO: 121) | 6 | 60 nM | 25 µl |

"FOL-001" consists of the following amino acid sequence:

```
VDVPNGRGDSLAYGLR      [SEQ ID NO: 121]
```

This sequence is a fragment of wildtype mouse osteopontin, and corresponds to the region of the protein from which "FOL-004" is derived (i.e. "FOL-004" is a mutated version of wildtype fragment "FOL-001").

Animals were administered the specified treatment on Days 1, 5 and 9

Treatment were administered by subcutaneous injection into dorsal clipped skin

Scoring Criteria

The effect of the treatments was observed and scored daily as described in Example B.

Results

Figure 6:
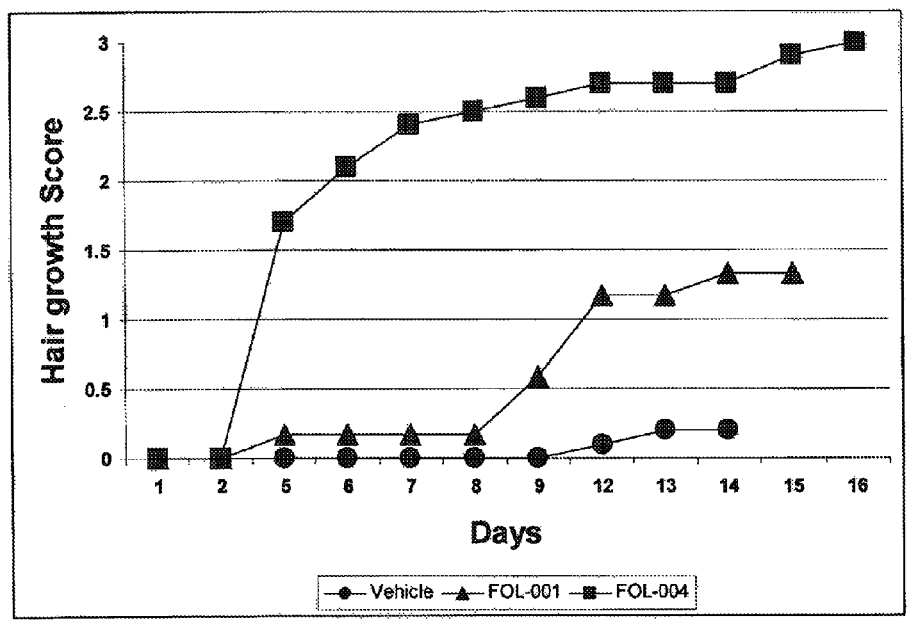
FIG. 6 shows the effect of exemplary polypeptide SEQ ID NO: 5 on hair growth, as compared to the corresponding polypeptide SEQ ID NO: 121 from wildtype mouse osteopontin.

The effect of the polypeptide "FOL-001" on hair growth is shown in Table 7 and FIG. 6.

TABLE 7

| Animal | Day | | | | | | | | | | |
|---|---|---|---|---|---|---|---|---|---|---|---|
| | 1 | 2 | 5 | 6 | 7 | 8 | 9 | 12 | 13 | 14 | 15 | 16 |
| FOL-001 (SEQ ID NO: 121, 60 nM) | | | | | | | | | | | |
| 1 | 0 | 0 | 0.5 | 0.5 | 0.5 | 0.5 | 1 | 2 | 2 | 2.5 | 2.5 | NA |
| 2 | 0 | 0 | 0.5 | 0.5 | 0.5 | 0.5 | 1 | 2 | 2 | 2.5 | 2.5 | NA |
| 3 | 0 | 0 | 0 | 0 | 0 | 0 | 0.5 | 1 | 1 | 1 | 1 | NA |
| 4 | 0 | 0 | 0 | 0 | 0 | 0 | 0 | 0 | 0 | 0 | 0 | NA |
| 5 | 0 | 0 | 0 | 0 | 0 | 0 | 0.5 | 1 | 1 | 1 | 1 | NA |
| 6 | 0 | 0 | 0 | 0 | 0 | 0 | 0.5 | 1 | 1 | 1 | 1 | NA |
| Mean | 0 | 0 | 0.17 | 0.17 | 0.17 | 0.17 | 0.58 | 1.17 | 1.17 | 1.33 | 1.33 | — |

Peptide FOL-001 (SEQ ID NO: 121) produced a delayed but detectable hair growth effect in mice, which became evident at about day 9 and reached a plateau at a score of about 1.3.

Conclusions

Compared to the corresponding mutated peptide sequence of the invention (FOL-004; SEQ ID NO:5), the equivalent non-mutated wild type sequence exhibited a delayed onset of hair growth stimulation with a maximum effect of less than 50% of that observed with FOL-004.

Thus, the exemplary polypeptide shows much greater efficacy than the equivalent non-mutated wild type sequence.

EXAMPLE D

In vivo Study of Anagen Induction in Peeled Skin

Materials and Methods

Animals and treatments are as described above in Example B.

All animals were sacrificed on day 16.

Observation of Melanogenesis

Following completion of the term of hair growth assessment for Example B, the animals were euthanized and dorsal skin peeled and removed for observation of the internal surface.

Histological Analysis

Peeled skin sections were prepared for histological analysis as described in Example A. Follicle count in the subcutis and skin thickness were then measured.

Results

Results are summarised in Tables 8 and 9 below.

TABLE 8

Observation of melanogenesis

| Group | Skin colour (external) | % anagen induction* | Black colour in peeled skin (day 16) | % anagen induction** | No. of animals showing hair growth |
|---|---|---|---|---|---|
| Cx (60 nM) | Black (5/5 animals) | 100 | 3/5 | 60 | 5/5 |
| FOL-004 (60 nM) | Black (5/5 animals) | 100 | 1/5 | 20 | 5/5 |
| FOL-005 (60 nM) | Black (5/5 animals) | 100 | 3/5 | 60 | 5/5 |
| Vehicle | Pink (4/5 animals) | 20 | 1/5 | 20 | 1/5 |

*with respect to external skin colour change from pink to black
**with respect to black colour in peeled skin TABLE 9a (all animals)

| Group | No. of animals considered | Mean ± sem | |
|---|---|---|---|
| | | Follicle count in subcutis (no.) | Skin thickness |
| Cx (60 nM) | 5 | 22.20 ± 10.69 | 308.8 ± 21.94 |
| FOL-004 (60 nM) | 5 | 6.20 ± 5.80 | 312.2 ± 15.60 |
| FOL-005 (60 nM) | 5 | 34.80 ± 14.58 | 348.80 ± 40.05 |
| Vehicle | 4* | 0 ± 0 | 246.5 ± 8.35 |

*Animal No. 5 was found to be a significant outlier ($p < 0/05$, Grubb's test) and so was ignored in analysis TABLE 9b (animals in anagen only)

| Group | No. of animals considered | Mean ± sem | |
|---|---|---|---|
| | | Follicle count in subcutis (no.) | Skin thickness |
| Cx (60 nM) | 3/5 | 36.67 ± 10.69 | 308.8 ± 21.94 |
| FOL-004 (60 nM) | 1/5 | 29 ± 5.8 | 312.2 ± 15.60 |
| FOL-005 (60 nM) | 3/5 | 58 ± 14.58 | 348.80 ± 40.05 |
| Vehicle | 0/4* | 0 ± 0 | 246.5 ± 8.35 |

The hair growth cycle consists of three phases: a resting telogen phase (C57BL/6 skin is a pale pink colour), an active hair growth anagen phase (where the skin becomes dark gray or black), and finally a catagen phase (where hair growth stops, and the skin transitions back to the telogen phase, returning to a pale pink colour).

In the present study, the animals were preselected for pink skin (telogen phase) and the test polypeptide was administered by subcutaneous/topical route. A good hair growth promoter triggers the transition from the resting telogen phase to the active anagen phase, and thus a transition from light skin to dark skin. This dark pigmentation may result from the collection of melanin in the hair follicles, in preparation for new hair growth during the anagen phase. Melanin synthesis of follicular melanocytes is strictly coupled to the anagen phase, ceases during catagen and is absent in telogen phase. Hence a good hair growth promoter causes blackening of dorsal skin. Upon termination, the dorsal skin of the animals was then excised out by peeling and the peeled skin reversed and observed for the induction of melanogenesis indicated by visual blackening. Histological analysis reveals number of follicles and skin thickness. A good hair growth promoter increases no. of follicles in sub cutis and skin thickness.

In the present study, all three test polypeptides led to the appearance of dense hair growth after three subcutaneous injections (see Example B above). It was also observed that in some of the animals, subsequent to full growth of the hair, the skin colour changed from black to gray to pink, a characteristic of catagen phase. The peeled skin collected in the study showed the black patch, indicative of anagen phase (active phase) of hair growth cycle due to melanocyte sequestering. In these animals, the histological results showed a large number of hair follicles and increase in skin thickness. But in some animals, where the catagen phase had occurred, peeled skin was found to be of pink colour, even though the hair coat was intact. Thus, analysis of such peeled skin sections demonstrated lack of follicles in subcutis but still good increase in skin thickness.

CONCLUSIONS

The exemplary mutated osteopontin polypeptides of the invention showed pronounced induction of anagen, as evidenced by an increase in the number of hair follicles in the subcutis and/or enhanced skin thickness.

SEQUENCE LISTING

```
<160> NUMBER OF SEQ ID NOS: 123

<210> SEQ ID NO 1
<211> LENGTH: 293
<212> TYPE: PRT
<213> ORGANISM: Artificial Sequence
<220> FEATURE:
<223> OTHER INFORMATION: Modified osteopontin

<400> SEQUENCE: 1

Met Arg Leu Ala Val Ile Cys Phe Cys Leu Phe Gly Ile Ala Ser Ser
1               5                   10                  15

Leu Pro Val Lys Val Thr Asp Ser Gly Ser Ser Glu Glu Lys Leu Tyr
            20                  25                  30

Ser Leu His Pro Asp Pro Ile Ala Thr Trp Leu Val Pro Asp Pro Ser
        35                  40                  45

Gln Lys Gln Asn Leu Leu Ala Pro Gln Asn Ala Val Ser Ser Glu Glu
    50                  55                  60

Lys Asp Asp Phe Lys Gln Glu Thr Leu Pro Ser Asn Ser Asn Glu Ser
65                  70                  75                  80

His Asp His Met Asp Asp Asp Asp Asp Asp Asp Asp Asp Asp Gly Asp
                85                  90                  95

His Ala Glu Ser Glu Asp Ser Val Asp Ser Asp Glu Ser Asp Glu Ser
            100                 105                 110

His His Ser Asp Glu Ser Asp Glu Thr Val Thr Ala Ser Thr Gln Ala
        115                 120                 125

Asp Thr Phe Thr Pro Ile Val Pro Thr Val Asp Val Pro Asn Gly Asp
    130                 135                 140

Ile Ser Leu Ala Tyr Gly Leu Arg Ser Lys Ser Arg Ser Phe Gln Val
145                 150                 155                 160

Ser Asp Glu Gln Tyr Pro Asp Ala Thr Asp Glu Asp Leu Thr Ser His
                165                 170                 175

Met Lys Ser Gly Glu Ser Lys Glu Ser Leu Asp Val Ile Pro Val Ala
            180                 185                 190

Gln Leu Leu Ser Met Pro Ser Asp Gln Asp Asn Asn Gly Lys Gly Ser
        195                 200                 205

His Glu Ser Ser Gln Leu Asp Glu Pro Ser Leu Glu Thr His Arg Leu
```

```
            210                 215                 220
Glu His Ser Lys Glu Ser Gln Glu Ser Ala Asp Gln Ser Asp Val Ile
225                 230                 235                 240

Asp Ser Gln Ala Ser Ser Lys Ala Ser Leu Glu His Gln Ser His Lys
                245                 250                 255

Phe His Ser His Lys Asp Lys Leu Val Leu Asp Pro Lys Ser Lys Glu
                260                 265                 270

Asp Asp Arg Tyr Leu Lys Phe Arg Ile Ser His Glu Leu Glu Ser Ser
                275                 280                 285

Ser Ser Glu Val Asn
    290

<210> SEQ ID NO 2
<211> LENGTH: 10
<212> TYPE: PRT
<213> ORGANISM: Artificial Sequence
<220> FEATURE:
<223> OTHER INFORMATION: Inactivated RGD domain

<400> SEQUENCE: 2

Asp Ile Ser Leu Ala Tyr Gly Leu Arg Ser
1               5                   10

<210> SEQ ID NO 3
<211> LENGTH: 299
<212> TYPE: PRT
<213> ORGANISM: Artificial Sequence
<220> FEATURE:
<223> OTHER INFORMATION: Modified osteopontin

<400> SEQUENCE: 3

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
                20                  25                  30

Tyr Asn Lys Tyr Pro Asp Ala Val Ala Thr Trp Leu Asn Pro Asp Pro
            35                  40                  45

Ser Gln Lys Gln Asn Leu Leu Ala Pro Gln Thr Leu Pro Ser Lys Ser
        50                  55                  60

Asn Glu Ser His Asp His Met Asp Asp Met Asp Asp Glu Asp Asp Asp
65                  70                  75                  80

Asp His Val Asp Ser Gln Asp Ser Ile Asp Ser Asn Asp Ser Asp Asp
                85                  90                  95

Val Asp Asp Thr Asp Asp Ser His Gln Ser Asp Glu Ser His His Ser
                100                 105                 110

Asp Glu Ser Asp Glu Leu Val Thr Asp Phe Pro Thr Asp Leu Pro Ala
            115                 120                 125

Thr Glu Val Phe Thr Pro Val Val Pro Thr Val Asp Thr Tyr Asp Gly
        130                 135                 140

Asp Ile Ser Val Val Tyr Gly Leu Arg Ser Lys Ser Lys Lys Phe Arg
145                 150                 155                 160

Arg Pro Asp Ile Gln Tyr Pro Asp Ala Thr Asp Glu Asp Ile Thr Ser
                165                 170                 175

His Met Glu Ser Glu Glu Leu Asn Gly Ala Tyr Lys Ala Ile Pro Val
            180                 185                 190

Ala Gln Asp Leu Asn Ala Pro Ser Asp Trp Asp Ser Arg Gly Lys Asp
        195                 200                 205
```

-continued

Ser Tyr Glu Thr Ser Gln Leu Asp Asp Gln Ser Ala Glu Thr His Ser
    210                 215                 220

His Lys Gln Ser Arg Leu Tyr Lys Arg Lys Ala Asn Asp Glu Ser Asn
225                 230                 235                 240

Glu His Ser Asp Val Ile Asp Ser Gln Glu Leu Ser Lys Val Ser Arg
                245                 250                 255

Glu Phe His Ser His Glu Phe His Ser His Glu Asp Met Leu Val Val
                260                 265                 270

Asp Pro Lys Ser Lys Glu Asp Lys His Leu Lys Phe Arg Ile Ser
            275                 280                 285

His Glu Leu Asp Ser Ala Ser Ser Glu Val Asn
    290                 295

<210> SEQ ID NO 4
<211> LENGTH: 10
<212> TYPE: PRT
<213> ORGANISM: Artificial Sequence
<220> FEATURE:
<223> OTHER INFORMATION: Inactivated RGD domain

<400> SEQUENCE: 4

Asp Ile Ser Val Val Tyr Gly Leu Arg Ser
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Preferred 15-amino acid peptide (FOL-004)

<400> SEQUENCE: 5

Val Asp Val Pro Asn Gly Asp Ile Ser Leu Ala Tyr Gly Leu Arg
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Preferred 15-amino acid peptide

<400> SEQUENCE: 6

Asp Val Pro Asn Gly Asp Ile Ser Leu Ala Tyr Gly Leu Arg Ser
1               5                   10                  15

<210> SEQ ID NO 7
<211> LENGTH: 14
<212> TYPE: PRT
<213> ORGANISM: Artificial Sequence
<220> FEATURE:
<223> OTHER INFORMATION: Preferred 14-amino acid peptide

<400> SEQUENCE: 7

Val Asp Val Pro Asn Gly Asp Ile Ser Leu Ala Tyr Gly Leu
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Preferred 14-amino acid peptide

<400> SEQUENCE: 8

```
Asp Val Pro Asn Gly Asp Ile Ser Leu Ala Tyr Gly Leu Arg
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Preferred 14-amino acid peptide

<400> SEQUENCE: 9

Val Pro Asn Gly Asp Ile Ser Leu Ala Tyr Gly Leu Arg Ser
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Preferred 13-amino acid peptide

<400> SEQUENCE: 10

Val Asp Val Pro Asn Gly Asp Ile Ser Leu Ala Tyr Gly
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Preferred 13-amino acid peptide

<400> SEQUENCE: 11

Asp Val Pro Asn Gly Asp Ile Ser Leu Ala Tyr Gly Leu
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Preferred 13-amino acid peptide

<400> SEQUENCE: 12

Val Pro Asn Gly Asp Ile Ser Leu Ala Tyr Gly Leu Arg
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Preferred 13-amino acid peptide

<400> SEQUENCE: 13

Pro Asn Gly Asp Ile Ser Leu Ala Tyr Gly Leu Arg Ser
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Preferred 12-amino acid peptide

<400> SEQUENCE: 14
```

-continued

```
Val Asp Val Pro Asn Gly Asp Ile Ser Leu Ala Tyr
1               5                   10
```

<210> SEQ ID NO 15
<211> LENGTH: 12
<212> TYPE: PRT
<213> ORGANISM: Artificial Sequence
<220> FEATURE:
<223> OTHER INFORMATION: Preferred 12-amino acid peptide

<400> SEQUENCE: 15

```
Asp Val Pro Asn Gly Asp Ile Ser Leu Ala Tyr Gly
1               5                   10
```

<210> SEQ ID NO 16
<211> LENGTH: 12
<212> TYPE: PRT
<213> ORGANISM: Artificial Sequence
<220> FEATURE:
<223> OTHER INFORMATION: Preferred 12-amino acid peptide

<400> SEQUENCE: 16

```
Val Pro Asn Gly Asp Ile Ser Leu Ala Tyr Gly Leu
1               5                   10
```

<210> SEQ ID NO 17
<211> LENGTH: 12
<212> TYPE: PRT
<213> ORGANISM: Artificial Sequence
<220> FEATURE:
<223> OTHER INFORMATION: Preferred 12-amino acid peptide

<400> SEQUENCE: 17

```
Pro Asn Gly Asp Ile Ser Leu Ala Tyr Gly Leu Arg
1               5                   10
```

<210> SEQ ID NO 18
<211> LENGTH: 12
<212> TYPE: PRT
<213> ORGANISM: Artificial Sequence
<220> FEATURE:
<223> OTHER INFORMATION: Preferred 12-amino acid peptide

<400> SEQUENCE: 18

```
Asn Gly Asp Ile Ser Leu Ala Tyr Gly Leu Arg Ser
1               5                   10
```

<210> SEQ ID NO 19
<211> LENGTH: 11
<212> TYPE: PRT
<213> ORGANISM: Artificial Sequence
<220> FEATURE:
<223> OTHER INFORMATION: Preferred 11-amino acid peptide

<400> SEQUENCE: 19

```
Val Asp Val Pro Asn Gly Asp Ile Ser Leu Ala
1               5                   10
```

<210> SEQ ID NO 20
<211> LENGTH: 11
<212> TYPE: PRT
<213> ORGANISM: Artificial Sequence
<220> FEATURE:
<223> OTHER INFORMATION: Preferred 11-amino acid peptide

<400> SEQUENCE: 20

```
Asp Val Pro Asn Gly Asp Ile Ser Leu Ala Tyr
```

```
<210> SEQ ID NO 21
<211> LENGTH: 11
<212> TYPE: PRT
<213> ORGANISM: Artificial Sequence
<220> FEATURE:
<223> OTHER INFORMATION: Preferred 11-amino acid peptide

<400> SEQUENCE: 21

Val Pro Asn Gly Asp Ile Ser Leu Ala Tyr Gly
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Preferred 11-amino acid peptide

<400> SEQUENCE: 22

Pro Asn Gly Asp Ile Ser Leu Ala Tyr Gly Leu
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Preferred 11-amino acid peptide

<400> SEQUENCE: 23

Asn Gly Asp Ile Ser Leu Ala Tyr Gly Leu Arg
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Preferred 11-amino acid peptide

<400> SEQUENCE: 24

Gly Asp Ile Ser Leu Ala Tyr Gly Leu Arg Ser
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Preferred 10-amino acid peptide

<400> SEQUENCE: 25

Val Asp Val Pro Asn Gly Asp Ile Ser Leu
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Preferred 10-amino acid peptide

<400> SEQUENCE: 26

Asp Val Pro Asn Gly Asp Ile Ser Leu Ala
1               5                   10
```

<210> SEQ ID NO 27
<211> LENGTH: 10
<212> TYPE: PRT
<213> ORGANISM: Artificial Sequence
<220> FEATURE:
<223> OTHER INFORMATION: Preferred 10-amino acid peptide

<400> SEQUENCE: 27

Val Pro Asn Gly Asp Ile Ser Leu Ala Tyr
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Preferred 10-amino acid peptide

<400> SEQUENCE: 28

Pro Asn Gly Asp Ile Ser Leu Ala Tyr Gly
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Preferred 10-amino acid peptide

<400> SEQUENCE: 29

Asn Gly Asp Ile Ser Leu Ala Tyr Gly Leu
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Preferred 10-amino acid peptide

<400> SEQUENCE: 30

Gly Asp Ile Ser Leu Ala Tyr Gly Leu Arg
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Preferred 10-amino acid peptide

<400> SEQUENCE: 31

Asp Ile Ser Leu Ala Tyr Gly Leu Arg Ser
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Preferred 9-amino acid peptide

<400> SEQUENCE: 32

Val Asp Val Pro Asn Gly Asp Ile Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Preferred 9-amino acid peptide

<400> SEQUENCE: 33

Asp Val Pro Asn Gly Asp Ile Ser Leu
1               5

<210> SEQ ID NO 34
<211> LENGTH: 9
<212> TYPE: PRT
<213> ORGANISM: Artificial Sequence
<220> FEATURE:
<223> OTHER INFORMATION: Preferred 9-amino acid peptide

<400> SEQUENCE: 34

Val Pro Asn Gly Asp Ile Ser Leu Ala
1               5

<210> SEQ ID NO 35
<211> LENGTH: 9
<212> TYPE: PRT
<213> ORGANISM: Artificial Sequence
<220> FEATURE:
<223> OTHER INFORMATION: Preferred 9-amino acid peptide

<400> SEQUENCE: 35

Pro Asn Gly Asp Ile Ser Leu Ala Tyr
1               5

<210> SEQ ID NO 36
<211> LENGTH: 9
<212> TYPE: PRT
<213> ORGANISM: Artificial Sequence
<220> FEATURE:
<223> OTHER INFORMATION: Preferred 9-amino acid peptide

<400> SEQUENCE: 36

Asn Gly Asp Ile Ser Leu Ala Tyr Gly
1               5

<210> SEQ ID NO 37
<211> LENGTH: 9
<212> TYPE: PRT
<213> ORGANISM: Artificial Sequence
<220> FEATURE:
<223> OTHER INFORMATION: Preferred 9-amino acid peptide

<400> SEQUENCE: 37

Gly Asp Ile Ser Leu Ala Tyr Gly Leu
1               5

<210> SEQ ID NO 38
<211> LENGTH: 9
<212> TYPE: PRT
<213> ORGANISM: Artificial Sequence
<220> FEATURE:
<223> OTHER INFORMATION: Preferred 9-amino acid peptide

<400> SEQUENCE: 38

Asp Ile Ser Leu Ala Tyr Gly Leu Arg
1               5

-continued

```
<210> SEQ ID NO 39
<211> LENGTH: 9
<212> TYPE: PRT
<213> ORGANISM: Artificial Sequence
<220> FEATURE:
<223> OTHER INFORMATION: Preferred 9-amino acid peptide

<400> SEQUENCE: 39

Ile Ser Leu Ala Tyr Gly Leu Arg Ser
1               5

<210> SEQ ID NO 40
<211> LENGTH: 8
<212> TYPE: PRT
<213> ORGANISM: Artificial Sequence
<220> FEATURE:
<223> OTHER INFORMATION: Preferred 8-amino acid peptide

<400> SEQUENCE: 40

Val Asp Val Pro Asn Gly Asp Ile
1               5

<210> SEQ ID NO 41
<211> LENGTH: 8
<212> TYPE: PRT
<213> ORGANISM: Artificial Sequence
<220> FEATURE:
<223> OTHER INFORMATION: Preferred 8-amino acid peptide

<400> SEQUENCE: 41

Asp Val Pro Asn Gly Asp Ile Ser
1               5

<210> SEQ ID NO 42
<211> LENGTH: 8
<212> TYPE: PRT
<213> ORGANISM: Artificial Sequence
<220> FEATURE:
<223> OTHER INFORMATION: Preferred 8-amino acid peptide

<400> SEQUENCE: 42

Val Pro Asn Gly Asp Ile Ser Leu
1               5

<210> SEQ ID NO 43
<211> LENGTH: 8
<212> TYPE: PRT
<213> ORGANISM: Artificial Sequence
<220> FEATURE:
<223> OTHER INFORMATION: Preferred 8-amino acid peptide

<400> SEQUENCE: 43

Pro Asn Gly Asp Ile Ser Leu Ala
1               5

<210> SEQ ID NO 44
<211> LENGTH: 8
<212> TYPE: PRT
<213> ORGANISM: Artificial Sequence
<220> FEATURE:
<223> OTHER INFORMATION: Preferred 8-amino acid peptide

<400> SEQUENCE: 44

Asn Gly Asp Ile Ser Leu Ala Tyr
1               5

<210> SEQ ID NO 45
```

```
<211> LENGTH: 8
<212> TYPE: PRT
<213> ORGANISM: Artificial Sequence
<220> FEATURE:
<223> OTHER INFORMATION: Preferred 8-amino acid peptide

<400> SEQUENCE: 45

Gly Asp Ile Ser Leu Ala Tyr Gly
1               5

<210> SEQ ID NO 46
<211> LENGTH: 8
<212> TYPE: PRT
<213> ORGANISM: Artificial Sequence
<220> FEATURE:
<223> OTHER INFORMATION: Preferred 8-amino acid peptide

<400> SEQUENCE: 46

Asp Ile Ser Leu Ala Tyr Gly Leu
1               5

<210> SEQ ID NO 47
<211> LENGTH: 8
<212> TYPE: PRT
<213> ORGANISM: Artificial Sequence
<220> FEATURE:
<223> OTHER INFORMATION: Preferred 8-amino acid peptide

<400> SEQUENCE: 47

Ile Ser Leu Ala Tyr Gly Leu Arg
1               5

<210> SEQ ID NO 48
<211> LENGTH: 7
<212> TYPE: PRT
<213> ORGANISM: Artificial Sequence
<220> FEATURE:
<223> OTHER INFORMATION: Preferred 7-amino acid peptide

<400> SEQUENCE: 48

Val Asp Val Pro Asn Gly Asp
1               5

<210> SEQ ID NO 49
<211> LENGTH: 7
<212> TYPE: PRT
<213> ORGANISM: Artificial Sequence
<220> FEATURE:
<223> OTHER INFORMATION: Preferred 7-amino acid peptide

<400> SEQUENCE: 49

Asp Val Pro Asn Gly Asp Ile
1               5

<210> SEQ ID NO 50
<211> LENGTH: 7
<212> TYPE: PRT
<213> ORGANISM: Artificial Sequence
<220> FEATURE:
<223> OTHER INFORMATION: Preferred 7-amino acid peptide

<400> SEQUENCE: 50

Val Pro Asn Gly Asp Ile Ser
1               5

<210> SEQ ID NO 51
<211> LENGTH: 7
```

```
<212> TYPE: PRT
<213> ORGANISM: Artificial Sequence
<220> FEATURE:
<223> OTHER INFORMATION: Preferred 7-amino acid peptide

<400> SEQUENCE: 51

Pro Asn Gly Asp Ile Ser Leu
1               5

<210> SEQ ID NO 52
<211> LENGTH: 7
<212> TYPE: PRT
<213> ORGANISM: Artificial Sequence
<220> FEATURE:
<223> OTHER INFORMATION: Preferred 7-amino acid peptide

<400> SEQUENCE: 52

Asn Gly Asp Ile Ser Leu Ala
1               5

<210> SEQ ID NO 53
<211> LENGTH: 7
<212> TYPE: PRT
<213> ORGANISM: Artificial Sequence
<220> FEATURE:
<223> OTHER INFORMATION: Preferred 7-amino acid peptide

<400> SEQUENCE: 53

Gly Asp Ile Ser Leu Ala Tyr
1               5

<210> SEQ ID NO 54
<211> LENGTH: 7
<212> TYPE: PRT
<213> ORGANISM: Artificial Sequence
<220> FEATURE:
<223> OTHER INFORMATION: Preferred 7-amino acid peptide

<400> SEQUENCE: 54

Asp Ile Ser Leu Ala Tyr Gly
1               5

<210> SEQ ID NO 55
<211> LENGTH: 7
<212> TYPE: PRT
<213> ORGANISM: Artificial Sequence
<220> FEATURE:
<223> OTHER INFORMATION: Preferred 7-amino acid peptide

<400> SEQUENCE: 55

Ile Ser Leu Ala Tyr Gly Leu
1               5

<210> SEQ ID NO 56
<211> LENGTH: 6
<212> TYPE: PRT
<213> ORGANISM: Artificial Sequence
<220> FEATURE:
<223> OTHER INFORMATION: Preferred 6-amino acid peptide

<400> SEQUENCE: 56

Asp Val Pro Asn Gly Asp
1               5

<210> SEQ ID NO 57
<211> LENGTH: 6
<212> TYPE: PRT
```

<213> ORGANISM: Artificial Sequence
<220> FEATURE:
<223> OTHER INFORMATION: Preferred 6-amino acid peptide

<400> SEQUENCE: 57

Val Pro Asn Gly Asp Ile
1               5

<210> SEQ ID NO 58
<211> LENGTH: 6
<212> TYPE: PRT
<213> ORGANISM: Artificial Sequence
<220> FEATURE:
<223> OTHER INFORMATION: Preferred 6-amino acid peptide

<400> SEQUENCE: 58

Pro Asn Gly Asp Ile Ser
1               5

<210> SEQ ID NO 59
<211> LENGTH: 6
<212> TYPE: PRT
<213> ORGANISM: Artificial Sequence
<220> FEATURE:
<223> OTHER INFORMATION: Preferred 6-amino acid peptide

<400> SEQUENCE: 59

Asn Gly Asp Ile Ser Leu
1               5

<210> SEQ ID NO 60
<211> LENGTH: 6
<212> TYPE: PRT
<213> ORGANISM: Artificial Sequence
<220> FEATURE:
<223> OTHER INFORMATION: Preferred 6-amino acid peptide

<400> SEQUENCE: 60

Gly Asp Ile Ser Leu Ala
1               5

<210> SEQ ID NO 61
<211> LENGTH: 6
<212> TYPE: PRT
<213> ORGANISM: Artificial Sequence
<220> FEATURE:
<223> OTHER INFORMATION: Preferred 6-amino acid peptide

<400> SEQUENCE: 61

Asp Ile Ser Leu Ala Tyr
1               5

<210> SEQ ID NO 62
<211> LENGTH: 6
<212> TYPE: PRT
<213> ORGANISM: Artificial Sequence
<220> FEATURE:
<223> OTHER INFORMATION: Preferred 6-amino acid peptide

<400> SEQUENCE: 62

Ile Ser Leu Ala Tyr Gly
1               5

<210> SEQ ID NO 63
<211> LENGTH: 15
<212> TYPE: PRT
<213> ORGANISM: Artificial Sequence
<220> FEATURE:
<223> OTHER INFORMATION: Preferred 15-amino acid peptide

<400> SEQUENCE: 63

Val Asp Thr Tyr Asp Gly Asp Ile Ser Val Val Tyr Gly Leu Arg
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Preferred 15-amino acid peptide

<400> SEQUENCE: 64

Val Asp Thr Tyr Asp Gly Asp Ile Ser Val Val Tyr Gly Leu Ser
1               5                   10                  15

<210> SEQ ID NO 65
<211> LENGTH: 14
<212> TYPE: PRT
<213> ORGANISM: Artificial Sequence
<220> FEATURE:
<223> OTHER INFORMATION: Preferred 14-amino acid peptide

<400> SEQUENCE: 65

Val Asp Thr Tyr Asp Gly Asp Ile Ser Val Val Tyr Gly Leu
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Preferred 14-amino acid peptide

<400> SEQUENCE: 66

Asp Thr Tyr Asp Gly Asp Ile Ser Val Val Tyr Gly Leu Arg
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Preferred 14-amino acid peptide

<400> SEQUENCE: 67

Thr Tyr Asp Gly Asp Ile Ser Val Val Tyr Gly Leu Arg Ser
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Preferred 13-amino acid peptide

<400> SEQUENCE: 68

Val Asp Thr Tyr Asp Gly Asp Ile Ser Val Val Tyr Gly
1               5                   10

<210> SEQ ID NO 69
<211> LENGTH: 13
<212> TYPE: PRT
<213> ORGANISM: Artificial Sequence
<220> FEATURE:

```
<223> OTHER INFORMATION: Preferred 13-amino acid peptide

<400> SEQUENCE: 69

Asp Thr Tyr Asp Gly Asp Ile Ser Val Val Tyr Gly Leu
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Preferred 13-amino acid peptide

<400> SEQUENCE: 70

Thr Tyr Asp Gly Asp Ile Ser Val Val Tyr Gly Leu Arg
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Preferred 13-amino acid peptide

<400> SEQUENCE: 71

Tyr Asp Gly Asp Ile Ser Val Val Tyr Gly Leu Arg Ser
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Preferred 12-amino acid peptide

<400> SEQUENCE: 72

Val Asp Thr Tyr Asp Gly Asp Ile Ser Val Val Tyr
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Preferred 12-amino acid peptide

<400> SEQUENCE: 73

Asp Thr Tyr Asp Gly Asp Ile Ser Val Val Tyr Gly
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Preferred 12-amino acid peptide

<400> SEQUENCE: 74

Thr Tyr Asp Gly Asp Ile Ser Val Val Tyr Gly Leu
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Preferred 12-amino acid peptide
```

```
<400> SEQUENCE: 75

Tyr Asp Gly Asp Ile Ser Val Val Tyr Gly Leu Arg
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Preferred 12-amino acid peptide

<400> SEQUENCE: 76

Asp Gly Asp Ile Ser Val Val Tyr Gly Leu Arg Ser
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Preferred 11-amino acid peptide

<400> SEQUENCE: 77

Val Asp Thr Tyr Asp Gly Asp Ile Ser Val Val
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Preferred 11-amino acid peptide

<400> SEQUENCE: 78

Asp Thr Tyr Asp Gly Asp Ile Ser Val Val Tyr
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Preferred 11-amino acid peptide

<400> SEQUENCE: 79

Thr Tyr Asp Gly Asp Ile Ser Val Val Tyr Gly
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Preferred 11-amino acid peptide

<400> SEQUENCE: 80

Tyr Asp Gly Asp Ile Ser Val Val Tyr Gly Leu
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Preferred 11-amino acid peptide
```

```
<400> SEQUENCE: 81

Asp Gly Asp Ile Ser Val Val Tyr Gly Leu Arg
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Preferred 11-amino acid peptide

<400> SEQUENCE: 82

Gly Asp Ile Ser Val Val Tyr Gly Leu Arg Ser
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Preferred 10-amino acid peptide

<400> SEQUENCE: 83

Val Asp Thr Tyr Asp Gly Asp Ile Ser Val
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Preferred 10-amino acid peptide

<400> SEQUENCE: 84

Asp Thr Tyr Asp Gly Asp Ile Ser Val Val
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Preferred 10-amino acid peptide

<400> SEQUENCE: 85

Thr Tyr Asp Gly Asp Ile Ser Val Val Tyr
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Preferred 10-amino acid peptide

<400> SEQUENCE: 86

Tyr Asp Gly Asp Ile Ser Val Val Tyr Gly
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Preferred 10-amino acid peptide

<400> SEQUENCE: 87
```

Asp Gly Asp Ile Ser Val Val Tyr Gly Leu
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Preferred 10-amino acid peptide

<400> SEQUENCE: 88

Gly Asp Ile Ser Val Val Tyr Gly Leu Arg
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Preferred 10-amino acid peptide

<400> SEQUENCE: 89

Asp Ile Ser Val Val Tyr Gly Leu Arg Ser
1               5                   10

<210> SEQ ID NO 90
<211> LENGTH: 9
<212> TYPE: PRT
<213> ORGANISM: Artificial Sequence
<220> FEATURE:
<223> OTHER INFORMATION: Preferred 9-amino acid peptide

<400> SEQUENCE: 90

Val Asp Thr Tyr Asp Gly Asp Ile Ser
1               5

<210> SEQ ID NO 91
<211> LENGTH: 9
<212> TYPE: PRT
<213> ORGANISM: Artificial Sequence
<220> FEATURE:
<223> OTHER INFORMATION: Preferred 9-amino acid peptide

<400> SEQUENCE: 91

Asp Thr Tyr Asp Gly Asp Ile Ser Val
1               5

<210> SEQ ID NO 92
<211> LENGTH: 9
<212> TYPE: PRT
<213> ORGANISM: Artificial Sequence
<220> FEATURE:
<223> OTHER INFORMATION: Preferred 9-amino acid peptide

<400> SEQUENCE: 92

Thr Tyr Asp Gly Asp Ile Ser Val Val
1               5

<210> SEQ ID NO 93
<211> LENGTH: 9
<212> TYPE: PRT
<213> ORGANISM: Artificial Sequence
<220> FEATURE:
<223> OTHER INFORMATION: Preferred 9-amino acid peptide

<400> SEQUENCE: 93

Tyr Asp Gly Asp Ile Ser Val Val Tyr
1               5

<210> SEQ ID NO 94
<211> LENGTH: 9
<212> TYPE: PRT
<213> ORGANISM: Artificial Sequence
<220> FEATURE:
<223> OTHER INFORMATION: Preferred 9-amino acid peptide

<400> SEQUENCE: 94

Asp Gly Asp Ile Ser Val Val Tyr Gly
1               5

<210> SEQ ID NO 95
<211> LENGTH: 9
<212> TYPE: PRT
<213> ORGANISM: Artificial Sequence
<220> FEATURE:
<223> OTHER INFORMATION: Preferred 9-amino acid peptide

<400> SEQUENCE: 95

Gly Asp Ile Ser Val Val Tyr Gly Leu
1               5

<210> SEQ ID NO 96
<211> LENGTH: 9
<212> TYPE: PRT
<213> ORGANISM: Artificial Sequence
<220> FEATURE:
<223> OTHER INFORMATION: Preferred 9-amino acid peptide

<400> SEQUENCE: 96

Asp Ile Ser Val Val Tyr Gly Leu Arg
1               5

<210> SEQ ID NO 97
<211> LENGTH: 9
<212> TYPE: PRT
<213> ORGANISM: Artificial Sequence
<220> FEATURE:
<223> OTHER INFORMATION: Preferred 9-amino acid peptide

<400> SEQUENCE: 97

Ile Ser Val Val Tyr Gly Leu Arg Ser
1               5

<210> SEQ ID NO 98
<211> LENGTH: 8
<212> TYPE: PRT
<213> ORGANISM: Artificial Sequence
<220> FEATURE:
<223> OTHER INFORMATION: Preferred 8-amino acid peptide

<400> SEQUENCE: 98

Val Asp Thr Tyr Asp Gly Asp Ile
1               5

<210> SEQ ID NO 99
<211> LENGTH: 8
<212> TYPE: PRT
<213> ORGANISM: Artificial Sequence
<220> FEATURE:
<223> OTHER INFORMATION: Preferred 8-amino acid peptide

<400> SEQUENCE: 99

Asp Thr Tyr Asp Gly Asp Ile Ser

```
1               5
```

<210> SEQ ID NO 100
<211> LENGTH: 8
<212> TYPE: PRT
<213> ORGANISM: Artificial Sequence
<220> FEATURE:
<223> OTHER INFORMATION: Preferred 8-amino acid peptide

<400> SEQUENCE: 100

```
Thr Tyr Asp Gly Asp Ile Ser Val
1               5
```

<210> SEQ ID NO 101
<211> LENGTH: 8
<212> TYPE: PRT
<213> ORGANISM: Artificial Sequence
<220> FEATURE:
<223> OTHER INFORMATION: Preferred 8-amino acid peptide

<400> SEQUENCE: 101

```
Tyr Asp Gly Asp Ile Ser Val Val
1               5
```

<210> SEQ ID NO 102
<211> LENGTH: 8
<212> TYPE: PRT
<213> ORGANISM: Artificial Sequence
<220> FEATURE:
<223> OTHER INFORMATION: Preferred 8-amino acid peptide

<400> SEQUENCE: 102

```
Asp Gly Asp Ile Ser Val Val Tyr
1               5
```

<210> SEQ ID NO 103
<211> LENGTH: 8
<212> TYPE: PRT
<213> ORGANISM: Artificial Sequence
<220> FEATURE:
<223> OTHER INFORMATION: Preferred 8-amino acid peptide

<400> SEQUENCE: 103

```
Gly Asp Ile Ser Val Val Tyr Gly
1               5
```

<210> SEQ ID NO 104
<211> LENGTH: 8
<212> TYPE: PRT
<213> ORGANISM: Artificial Sequence
<220> FEATURE:
<223> OTHER INFORMATION: Preferred 8-amino acid peptide

<400> SEQUENCE: 104

```
Asp Ile Ser Val Val Tyr Gly Leu
1               5
```

<210> SEQ ID NO 105
<211> LENGTH: 8
<212> TYPE: PRT
<213> ORGANISM: Artificial Sequence
<220> FEATURE:
<223> OTHER INFORMATION: Preferred 8-amino acid peptide

<400> SEQUENCE: 105

```
Ile Ser Val Val Tyr Gly Leu Arg
1               5
```

<210> SEQ ID NO 106
<211> LENGTH: 7
<212> TYPE: PRT
<213> ORGANISM: Artificial Sequence
<220> FEATURE:
<223> OTHER INFORMATION: Preferred 7-amino acid peptide

<400> SEQUENCE: 106

Val Asp Thr Tyr Asp Gly Asp
1               5

<210> SEQ ID NO 107
<211> LENGTH: 7
<212> TYPE: PRT
<213> ORGANISM: Artificial Sequence
<220> FEATURE:
<223> OTHER INFORMATION: Preferred 7-amino acid peptide

<400> SEQUENCE: 107

Asp Thr Tyr Asp Gly Asp Ile
1               5

<210> SEQ ID NO 108
<211> LENGTH: 7
<212> TYPE: PRT
<213> ORGANISM: Artificial Sequence
<220> FEATURE:
<223> OTHER INFORMATION: Preferred 7-amino acid peptide

<400> SEQUENCE: 108

Thr Tyr Asp Gly Asp Ile Ser
1               5

<210> SEQ ID NO 109
<211> LENGTH: 7
<212> TYPE: PRT
<213> ORGANISM: Artificial Sequence
<220> FEATURE:
<223> OTHER INFORMATION: Preferred 7-amino acid peptide

<400> SEQUENCE: 109

Tyr Asp Gly Asp Ile Ser Val
1               5

<210> SEQ ID NO 110
<211> LENGTH: 7
<212> TYPE: PRT
<213> ORGANISM: Artificial Sequence
<220> FEATURE:
<223> OTHER INFORMATION: Preferred 7-amino acid peptide

<400> SEQUENCE: 110

Asp Gly Asp Ile Ser Val Val
1               5

<210> SEQ ID NO 111
<211> LENGTH: 7
<212> TYPE: PRT
<213> ORGANISM: Artificial Sequence
<220> FEATURE:
<223> OTHER INFORMATION: Preferred 7-amino acid peptide

<400> SEQUENCE: 111

Gly Asp Ile Ser Val Val Tyr
1               5

```
<210> SEQ ID NO 112
<211> LENGTH: 7
<212> TYPE: PRT
<213> ORGANISM: Artificial Sequence
<220> FEATURE:
<223> OTHER INFORMATION: Preferred 7-amino acid peptide

<400> SEQUENCE: 112

Asp Ile Ser Val Val Tyr Gly
1               5

<210> SEQ ID NO 113
<211> LENGTH: 7
<212> TYPE: PRT
<213> ORGANISM: Artificial Sequence
<220> FEATURE:
<223> OTHER INFORMATION: Preferred 7-amino acid peptide

<400> SEQUENCE: 113

Ile Ser Val Val Tyr Gly Leu
1               5

<210> SEQ ID NO 114
<211> LENGTH: 6
<212> TYPE: PRT
<213> ORGANISM: Artificial Sequence
<220> FEATURE:
<223> OTHER INFORMATION: Preferred 6-amino acid peptide

<400> SEQUENCE: 114

Asp Thr Tyr Asp Gly Asp
1               5

<210> SEQ ID NO 115
<211> LENGTH: 6
<212> TYPE: PRT
<213> ORGANISM: Artificial Sequence
<220> FEATURE:
<223> OTHER INFORMATION: Preferred 6-amino acid peptide

<400> SEQUENCE: 115

Thr Tyr Asp Gly Asp Ile
1               5

<210> SEQ ID NO 116
<211> LENGTH: 6
<212> TYPE: PRT
<213> ORGANISM: Artificial Sequence
<220> FEATURE:
<223> OTHER INFORMATION: Preferred 6-amino acid peptide

<400> SEQUENCE: 116

Tyr Asp Gly Asp Ile Ser
1               5

<210> SEQ ID NO 117
<211> LENGTH: 6
<212> TYPE: PRT
<213> ORGANISM: Artificial Sequence
<220> FEATURE:
<223> OTHER INFORMATION: Preferred 6-amino acid peptide

<400> SEQUENCE: 117

Asp Gly Asp Ile Ser Val
1               5
```

```
<210> SEQ ID NO 118
<211> LENGTH: 6
<212> TYPE: PRT
<213> ORGANISM: Artificial Sequence
<220> FEATURE:
<223> OTHER INFORMATION: Preferred 6-amino acid peptide

<400> SEQUENCE: 118

Gly Asp Ile Ser Val Val
1               5

<210> SEQ ID NO 119
<211> LENGTH: 6
<212> TYPE: PRT
<213> ORGANISM: Artificial Sequence
<220> FEATURE:
<223> OTHER INFORMATION: Preferred 6-amino acid peptide

<400> SEQUENCE: 119

Asp Ile Ser Val Val Tyr
1               5

<210> SEQ ID NO 120
<211> LENGTH: 6
<212> TYPE: PRT
<213> ORGANISM: Artificial Sequence
<220> FEATURE:
<223> OTHER INFORMATION: Preferred 6-amino acid peptide

<400> SEQUENCE: 120

Ile Ser Val Val Tyr Gly
1               5

<210> SEQ ID NO 121
<211> LENGTH: 16
<212> TYPE: PRT
<213> ORGANISM: Artificial Sequence
<220> FEATURE:
<223> OTHER INFORMATION: FOL-001

<400> SEQUENCE: 121

Val Asp Val Pro Asn Gly Arg Gly Asp Ser Leu Ala Tyr Gly Leu Arg
1               5                   10                  15

<210> SEQ ID NO 122
<211> LENGTH: 11
<212> TYPE: PRT
<213> ORGANISM: Homo sapiens

<400> SEQUENCE: 122

Arg Gly Asp Ser Leu Ala Tyr Gly Leu Arg Ser
1               5                   10

<210> SEQ ID NO 123
<211> LENGTH: 7
<212> TYPE: PRT
<213> ORGANISM: Homo sapiens

<400> SEQUENCE: 123

Ser Leu Ala Tyr Gly Leu Arg
1               5
```

The invention claimed is:

1. A composition for stimulating hair growth in a mammal comprising:
   (a) a modified osteopontin polypeptide selected from the group consisting of a polypeptide consisting of the amino acid sequence of SEQ ID NO: 1, a polypeptide consisting of the amino acid sequence of SEQ ID NO: 5, and a polypeptide consisting of the amino acid sequence of SEQ ID NO: 63; and
   (b) a pharmaceutically acceptable and/or cosmetically acceptable excipient, carrier or diluent.

2. A composition according to claim 1 wherein the polypeptide is capable of inducing the formation of new hair follicles.

3. A composition according to claim 1 wherein the modified osteopontin polypeptide consists of the amino acid sequence of SEQ ID NO: 1:

```
                                              SEQ ID NO: 1
MRLAVICFCLFGIASSLPVKVTDSGSSEEKLYSLHPDPIATWLVPDPSQK

QNLLAPQNAVSSEEKDDFKQETLPSNSNESHDHMDDDDDDDDDGD
```

-continued
```
HAESEDSVDSDESDESHHSDESDETVTASTQADTFTPIVPTVDVPNGD

ISLAYGLRSKSRSFQVSDEQYPDATDEDLTSHMKSGESKESLDVIPVAQ

LLSMPSDQDNNGKGSHESSQLDEPSLETHRLEHSKESQESADQSDVID

SQASSKASLEHQSHKFHSHKDKLVLDPKSKEDDRYLKFRISHELESSSS

EVN.
```

4. A composition according to claim 1 wherein the modified osteopontin polypeptide consists of the amino acid sequence of SEQ ID NO: 5.

5. A composition according to claim 1 wherein the modified osteopontin polypeptide consists of the amino acid sequence of SEQ ID NO: 63.

6. A composition according to claim 1 for transdermal administration.

7. A polypeptide consisting of the amino acid sequence of SEQ ID NO: 63.

8. A polypeptide consisting of the amino acid sequence of SEQ ID NO: 5.

* * * * *